(12) United States Patent
Maggio

(10) Patent No.: US 8,846,044 B2
(45) Date of Patent: *Sep. 30, 2014

(54) STABILIZING ALKYLGLYCOSIDE COMPOSITIONS AND METHODS THEREOF

(75) Inventor: Edward T. Maggio, San Diego, CA (US)

(73) Assignee: Aegis Therapeutics, LLC, San Diego, CA (US)

(*) Notice: Subject to any disclaimer, the term of this patent is extended or adjusted under 35 U.S.C. 154(b) by 156 days.

This patent is subject to a terminal disclaimer.

(21) Appl. No.: 13/544,851

(22) Filed: Jul. 9, 2012

(65) Prior Publication Data

US 2013/0039851 A1    Feb. 14, 2013

Related U.S. Application Data

(63) Continuation of application No. 12/618,558, filed on Nov. 13, 2009, now Pat. No. 8,226,949, which is a continuation-in-part of application No. 12/119,378, filed on May 12, 2008, now Pat. No. 7,998,927, which is a continuation-in-part of application No. 12/050,038, filed on Mar. 17, 2008, now Pat. No. 8,084,022, which is a continuation-in-part of application No. 11/474,055, filed on Jun. 23, 2006, now Pat. No. 7,425,542.

(51) Int. Cl.
*A61K 39/395* (2006.01)
*A61K 47/26* (2006.01)
*A61K 9/00* (2006.01)
*A61K 9/127* (2006.01)
*A61K 9/19* (2006.01)
*A61K 31/70* (2006.01)

(52) U.S. Cl.
CPC .............. *A61K 9/0043* (2013.01); *A61K 9/127* (2013.01); *A61K 9/19* (2013.01); *A61K 31/70* (2013.01); *A61K 47/26* (2013.01)
USPC ...................... 424/141.1; 424/142.1; 514/777

(58) Field of Classification Search
None
See application file for complete search history.

(56) References Cited

U.S. PATENT DOCUMENTS

| | | | |
|---|---|---|---|
| 4,130,709 A | 12/1978 | Nagarajan | |
| 4,440,675 A | 4/1984 | Braude | |
| 4,476,116 A | 10/1984 | Anik | |
| 5,122,187 A | 6/1992 | Schwarz et al. | |
| 5,198,420 A | 3/1993 | Donahoe et al. | |
| 5,369,095 A | 11/1994 | Kee et al. | |
| 5,556,757 A | 9/1996 | Alstyne et al. | |
| 5,556,940 A | 9/1996 | Willick et al. | |
| 5,661,130 A | 8/1997 | Meezan et al. | |
| 6,524,557 B1 | 2/2003 | Backstrom et al. | |
| 6,551,578 B2 | 4/2003 | Adjei et al. | |
| 7,425,542 B2 | 9/2008 | Maggio | |
| 7,998,927 B2 | 8/2011 | Maggio | |
| 8,226,949 B2* | 7/2012 | Maggio | 424/141.1 |
| 2002/0110524 A1 | 8/2002 | Cowan et al. | |
| 2004/0209814 A1 | 10/2004 | Nauck et al. | |
| 2005/0215475 A1 | 9/2005 | Ong et al. | |
| 2005/0276843 A1 | 12/2005 | Quay et al. | |
| 2006/0046962 A1 | 3/2006 | Meezan et al. | |
| 2006/0074025 A1 | 4/2006 | Quay et al. | |
| 2006/0084604 A1 | 4/2006 | Kitaura et al. | |
| 2006/0183674 A1 | 8/2006 | Brand et al. | |
| 2007/0111938 A1 | 5/2007 | Pert et al. | |
| 2008/0194461 A1 | 8/2008 | Maggio | |
| 2008/0268032 A1 | 10/2008 | Maggio | |
| 2009/0047347 A1 | 2/2009 | Maggio | |
| 2009/0156478 A1 | 6/2009 | Lau et al. | |
| 2009/0326193 A1 | 12/2009 | Maggio et al. | |

FOREIGN PATENT DOCUMENTS

WO  WO 2006/025882 A3  3/2006
WO  WO 2006/051110 A3  5/2006

OTHER PUBLICATIONS

Brown and Schonbrunn, "Affinity Purification of a Somatostatin Receptor-G-Protein Complex demonstrates Specificity in Receptor-G-Protein Coupling," *J. Biol. Chem.* (1993), 268(9):6668-6676, The American Society for Biochemistry and Molecular Biology, Inc.
Hovgaard et al., "Stabilization of Insulin by Alkylmaltosides. A. Spectroscopic Evaluation," *Int. J. Pharm.* (1996), 132:107-113, Elsevier Science B.V.
Hovgaard et al., "Stabilization of Insulin by Alkylmaltosides. B. Oral Absorption in vivo in Rats," *Int. J. Pharm.* (1996), 132:115-121, Elsevier Science B.V.
Mitrano and Newton, "Factors Affecting Insulin Adherence to Type I Glass Bottles," *Am. J. Hosp. Pharm.* (1982), 39(9):1491-1495.
van der Lubben et al., "Chitosan and its Derivatives in Mucosal Drug and Vaccine Delivery," *Eur. J. Pharm. Sci.* (2001) 14:201-207, Elsevier.
Ahsan et al., "Mutual inhibition of the insulin absorption-enhancing properties of dodecylmaltoside and dimethyl-beta-cyclodextrin following nasal administration", *Pharm Res.*, 18(5):608-14 (2001).
VanAken et al., "Alkyl glycoside detergents: synthesis and applications to the study of membrane proteins", *Methods Enzymol.*, 125:27-35 (1986).
Maggio E.T., "Intravail: highly effective intranasal delivery of peptide and protein drugs", *Expert Opin. Drug Deliv.*, 3(4):529-39 (2006).
European Search Report (ESR) from application No. EP 10 79 2685., completed Jul. 8, 2013.

\* cited by examiner

*Primary Examiner* — Jeffrey E Russel
(74) *Attorney, Agent, or Firm* — DLA Piper LLP (US)

(57) ABSTRACT

The present invention relates to alkylglycoside-containing compositions and methods for increasing the stability, reducing the aggregation and immunogenicity, increasing the biological activity, and reducing or preventing fibrillar formation of a peptide, polypeptide, or variant thereof, for example parathyroid hormone (PTH) or PTH analogs, amylin, a monoclonal antibody, insulin, Peptide T or analog thereof, gastrin, gastrin releasing peptides, gastrin releasing peptide-like (GRP) proteins, epidermal growth factor or analog thereof.

48 Claims, 15 Drawing Sheets

STABILIZING ALKYLGLYCOSIDE COMPOSITIONS AND METHODS THEREOF

CROSS-REFERENCE TO RELATED APPLICATIONS

This application is a continuation application of U.S. application Ser. No. 12/618,558 filed Nov. 13, 2009, now issued as U.S. Pat. No. 8,226,949; which is a continuation-in-part of U.S. application Ser. No. 12/119,378 filed May 12, 2008, now issued as U.S. Pat. No. 7,998,927; which is a continuation-in-part of application of U.S. application Ser. No. 12/050,038 filed Mar. 17, 2008, now issued as U.S. Pat. No. 8,084,022; which is a continuation-in-part of U.S. application Ser. No. 11/474,055 filed Jun. 23, 2006, now issued as U.S. Pat. No. 7,425,542. The disclosure of each of the prior applications is considered part of and is incorporated by reference in the disclosure of this application.

BACKGROUND OF THE INVENTION

1. Field of the Invention

The present invention relates generally to compositions that increase stability, reduce aggegation and immunogenicity, increase biological activity, and/or reduce or prevent fibrillar formation of peptides or proteins in therapeutically useful formulations, and specifically, to compositions having at least one peptide or protein and at least one alkylglycoside or saccharide alkyl ester surfactant.

2. Background Information

Proteins undergo numerous physical and chemical changes that affect potency and safety. Among these are aggregation, which includes dimerization, trimerization, and higher-order aggregates, plus crystallization and precipitation. Aggregation is rapidly emerging as a key issue underlying multiple deleterious effects for peptide or protein-based therapeutics, including loss of efficacy, altered pharmacokinetics, reduced stability or product shelf life, and induction of unwanted immunogenicity. In addition, bioavailability and pharmacokinetics of a self-associating peptide can be influenced by aggregate size and the ease of disruption of the non-covalent intermolecular interactions at the subcutaneous site. Hydrophobic aggregation mediated by seemingly innocuous solution formulation conditions can have a dramatic effect on the subcutaneous bioavailability and pharmacokinetics of a therapeutic peptide and in the extreme, can totally preclude its absorption (Clodfelter 1998). During the course of the manufacturing process, proteins are purified and concentrated using a variety of means. These means include ultrafiltration, affinity chromatography, selective absorption chromatography, ion exchange chromatography, lyophilization, dialysis, and precipitation or salting-out. Such concentration can lead to aggregation which in turn can increase the immunogenicity of the protein therapeutic. One means to avoid this problem is to work with the protein solutions at lower concentrations and correspondingly larger volumes. However, the need to work with larger volumes naturally introduces inefficiencies in the manufacturing process. During fill-and-finish operations, concentrated protein solutions squeeze through piston pumps, which imparts high-shear and mechanical stresses that cause denaturation and aggregation. By adding alkylglycosides as described in the present invention to the protein solutions during the course of purification and concentration by the means described above, aggregation can be reduced or eliminated, providing for greater efficiency in the manufacturing process, and providing for a final product which is desirably less immunogenic. The concentrations of alkylglycoside found to be effective in this application must be at least somewhat higher than the critical micelle concentration.

Many products are only effective when delivered by injection in relatively high concentration. Preventing aggregation has become a major issue for pharmaceutical formulators since the trend toward high-concentration solutions increases the likelihood of protein-protein interactions favoring aggregation. Thus, protein aggregation may impact biological product process yield and potency. Since aggregation is frequently mediated by higher temperatures, protein therapeutics require certain so-called "Cold Chain" handling requirements to guarantee a continuous chain of refrigerated temperatures during shipping and storage (DePalma Jan. 15, 2006). Cold chain requirements significantly increase the cost of storing and transporting drugs. The present invention mitigates and, in some cases, may eliminate the need for strict cold-chain maintenance.

Over the last five years, the FDA and other regulatory agencies have increased their scrutiny of aggregation events, and thus biopharmaceutical companies have increased their efforts to understand them. Of particular concern is the induction of unwanted immunogenicity. The immunogenicity of a self-associating peptide can be influenced by the formation of aggregates formed as a result of non-covalent intermolecular interactions. For example, interferon has been shown to aggregate resulting in an antibody response (Hermeling et al. 2006). The antibody response to erythropoietin has been shown to produce "pure red cell aplasia" in a number of patients receiving recombinant EPO, (Casadevall et al. 2002) which is potentially a life threatening side effect of EPO therapy. Insulin is well known to lose activity rapidly as a result of protein aggregation upon agitation at temperatures above those found upon refrigerated storage (Pezron et al. 2002; Sluzky et al. 1991). Aggregation of recombinant AAV2 results in reduced yield during purification and has deleterious effects on immunogenicity following in vivo administration (Wright 2005). Monoclonal antibody based therapeutics have also been shown to be subject to inactivation as a result of protein aggregation (King et al. 2002). The number of monoclonal antibodies in human clinical trials has been on the rise. Often monoclonal antibodies require relatively high dosing (in the 1 to 2 mg/kg range) whether administered in a hospital setting by i.v. administration or in an outpatient setting in a clinic or at home by a more convenient mode of delivery such as subcutaneous administration. Development of antibody formulations at high concentrations pose stability, manufacturing, and delivery challenges related to the propensity of antibodies to aggregate at the higher concentrations.

Recombinant human factor VIII (rFVIII), a multidomain glycoprotein is used in replacement therapy for treatment of hemophilia A. Unfortunately, 15%-30% of the treated patients develop inhibitory antibodies. The presence of aggregated protein in formulations is generally believed to enhance the antibody development response (Purohit et al. 2006).

Enzymes too are known to lose activity as a result of aggregation. For example thermal inactivation of urokinase occurs via aggregation (Porter et al. 1993).

In addition, hydrophobic aggregation mediated by seemingly innocuous solution formulation conditions can have a dramatic effect on the subcutaneous bioavailability and pharmacokinetics of a therapeutic peptide and in the extreme, can totally preclude its absorption (Clodfelter et al. 1998). Peptide or protein therapeutics are frequently formulated at high concentration so that the volume of the formulation that must be administered in order to achieve a therapeutically effective dose can be kept small thereby minimizing patient discomfort. Unfortunately, high protein or peptide concentrations often induce aggregation. In addition, protein aggregation can be induced by necessary excipients such as the antimicrobial preservative benzyl alcohol which are included to maintain product sterility (Roy et al. 2005).

Protein stabilization during lyophilization has also posed problems. Protein therapeutics frequently lose biological activity after lyophilization and reconstitution as a result of aggregate formation and precipitation. Several reconstitution medium additives have been found to result in a significant reduction of aggregation. These include sulfated polysaccharides, polyphosphates, amino acids and various surfactants, not including alkylglycosides (Zhang et al. 1995). In some cases, a combination of alcohols, organic solvents, such as in Fortical, Unigene's nasally delivered calcitonin product, may be used. Roccatano et al. (2002) have used trifluoroethanol mixtures to stabilize various polypeptides. Unfortunately, such agents may be harsh on mucosal tissue causing patient discomfort or local toxicity.

SUMMARY OF THE INVENTION

The present invention relates generally to compositions that stabilize, reduce aggregation and immunogenicity of peptides or proteins in therapeutically useful formulations. More specifically, the present invention provides therapeutic compositions comprising at least one self-associating, or self-aggregating peptide or protein and at least one surfactant, wherein the surfactant is comprised of at least one alkylglycoside and/or saccharide alkyl ester. Further, the present invention provides for compositions that when administered to a subject, preclude or reduce aggregation, that increase the shelf-life of a therapeutic or increase the range of conditions such as temperature and agitation that may be tolerated without causing harm to the functional properties of a protein or peptide.

Accordingly, in one aspect of the invention, there is provided a pharmaceutical composition for increasing the stability, reducing aggregation or reducing immunogenicity of a therapeutically active peptide, polypeptide or variant thereof including a stabilizing agent, wherein the stabilizing agent is at least one alkylglycoside. The peptide, polypeptide or variant thereof includes but is not limited to insulin or an analog thereof, interferon, a monoclonal antibody, erythropoietin, Peptide T or an analog thereof, D-alanine Peptide T amide (DAPTA), growth hormone, parathyroid hormone (PTH) or active fragments thereof, such as but not limited to PTH 1-31 (Ostabolin C™), PTH 1-34 and PTH 3-34, insulin, native or modified amylin, Hematide™, gastrin, gastrin releasing peptide (GRP), and gastrin releasing peptide-like proteins, epidermal growth factor (EGF), or glucagon-like peptide-1. The alkylglycoside includes but is not limited dodecyl maltoside, tridecyl maltoside, tetradecyl maltoside, sucrose mono-dodecanoate, sucrose mono-tridecanoate, and sucrose mono-tetradecanoate.

In one aspect of the invention, there is provided a pharmaceutical composition for increasing the stability, reducing aggregation and/or reducing immunogenicity of a therapeutically active antibody, such as a monoclonal antibody (e.g., IgG-3). In another aspect, the invention provides a method for increasing the stability, reducing aggregation, and/or reducing immunogenicity of a therapeutically active antibody, such as a monoclonal antibody (e.g., IgG-3) by admixing the monoclonal antibody with a stabilizing agent and optionally, a buffering agent, wherein the stabilizing agent is at least one alkylglycoside, and wherein the alkylglycoside increases the stability, reduces aggregation, and/or reduces immunogenicity of the monoclonal antibody.

In one aspect of the invention, there is provided a pharmaceutical composition comprising amylin and at least one alkylglycoside. In another aspect of the invention, there is provided a method for treatment of diabetes mellitus or hypoglycemia by administering to a subject, a pharmaceutical composition comprising amylin and at least one alkygylcoside. In another aspect of the invention, there is provided a method for treatment of obesity by administering to a subject, a pharmaceutical composition comprising amylin and at least one alkyglycoside. The alkylglycoside may be, for example, dodecyl maltoside, tridecyl maltoside, tetradecyl maltoside, sucrose mono-dodecanoate, sucrose mono-tridecanoate, and sucrose mono-tetradecanoate.

In another aspect of the invention, there is provided a method for increasing the stability of a therapeutically active peptide, polypeptide or variant thereof by admixing a therapeutically active peptide, polypeptide or variant thereof, a stabilizing agent and a buffering agent, wherein the stabilizing agent is at least one alkylglycoside surfactant, wherein the surfactant increases the stability of the therapeutically active peptide, polypeptide or variant thereof.

The invention also provides a method for reducing aggregation of a therapeutically active peptide, polypeptide or variant thereof by admixing a therapeutically active peptide, polypeptide or variant thereof, an aggregation reducing agent, wherein the stabilizing agent is at least one alkylglycoside surfactant, wherein the surfactant reduces aggregation of the therapeutically active peptide, polypeptide or variant thereof.

In yet another aspect of the invention, there is provided a method for reducing immunogenicity of a therapeutically active peptide, polypeptide or variant thereof upon administration to a vertebrate, by admixing a therapeutically active peptide, polypeptide or variant thereof, an immunogenicity reducing agent, wherein the immunogenicity reducing agent is at least one alkylglycoside or surfactant, wherein the surfactant reduces immunogenicity of the therapeutically active peptide, polypeptide or variant thereof.

In one aspect of the invention, there is a formulation for treating a subject having or at risk of having HIV, the formulation containing a prophylactically or therapeutically effective amount of a composition comprising D-alanine Peptide T amide (DAPTA), and at least one alkylglycoside to the subject.

In another aspect of the invention, there is an intranasal formulation for treating a subject having or at risk of having HIV, the intranasal formulation containing a prophylactically or therapeutically effective amount of a composition comprising D-alanine Peptide T amide (DAPTA), and at least one alkylglycoside to the subject.

Still, the invention provides a formulation for treating a subject having a CCR5-mediated disease, the formulation containing a prophylactically or therapeutically effective amount of a composition comprising D-alanine Peptide T amide (DAPTA) and at least one alkylglycoside.

Still, the invention provides an intranasal formulation for treating a subject having or at risk of having a CCR5-mediated disease, the intranasal formulation containing a prophylactically or therapeutically effective amount of a composition comprising D-alanine Peptide T amide (DAPTA) and at least one alkylglycoside.

In yet another aspect of the invention, there is provided a method of treating a subject having or at risk of having HIV by administering a prophylactically or therapeutically effective amount of a composition comprising D-alanine Peptide T amide (DAPTA) and at least one alkylglycoside surfactant to the subject, thereby treating the subject.

The present invention also provides a method for treating an inflammatory disease by administering to a subject in need thereof a therapeutically effective amount of a therapeutically active peptide, polypeptide or variant composition containing a therapeutically active peptide or polypeptide or variant thereof, a stabilizing agent, and a buffering agent, wherein the stabilizing agent is at least one alkylglycoside, wherein the therapeutically active peptide, polypeptide or variant thereof is a Peptide T or analog thereof.

Another aspect of the invention is a method of manufacturing non-aggregated aqueous solutions of otherwise self-aggregating therapeutically active peptide, polypeptide or variant thereof by admixing at least one alkylglycoside surfactant in an aqueous solution of the self-aggregating therapeutically active peptide, polypeptide or variant thereof and concentrating the therapeutically active peptide, polypeptide or variant thereof.

DETAILED DESCRIPTION OF THE INVENTION

Figure 1:
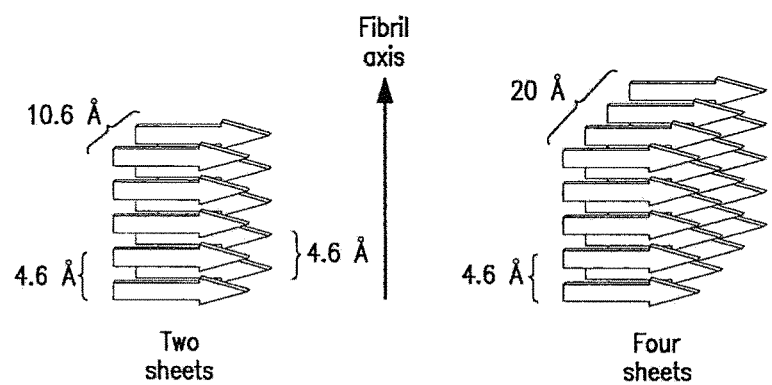
FIG. 1 is a diagram showing ordered fibrillar peptide aggregates packed in narrow parallel arrays of β sheets and stacked perpendicular to the long axis of the fibril.

The present invention may be understood more readily by reference to the following detailed description of specific embodiments and the Examples included therein.

The present invention describes formulations comprising at least one peptide or protein, whether at high or low concentration, and at least one alkylglycoside and/or saccharide alkyl ester surfactant, hereinafter termed "alkylglycosides". As used herein, "alkylglycoside" refers to any sugar joined by a linkage to any hydrophobic alkyl, as is known in the art. The linkage between the hydrophobic alkyl chain and the hydrophilic saccharide can include, among other possibilities, a glycosidic, ester, thioglycosidic, thioester, ether, amide or ureide bond or linkage. Examples of which are described herein. The terms alkylglycoside and alkylsaccharide may be used interchangeably herein.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference in their entirety.

The term, "stabilizing agent" or "stabilizer" as used herein is a chemical or compound that is added to a solution or mixture or suspension or composition or therapeutic composition to maintain it in a stable or unchanging state; or is one which is used because it produces a reaction involving changes in atoms or molecules leading to a more stable or unchanging state.

The term "aggregate" or "aggregation" as used herein is means to come together or collect in a mass or whole, e.g., as in the aggregation of peptides, polypeptides, or variants thereof. Aggregates can be self-aggregating or aggregate due to other factors, e.g., aggregating agents or precipitating agents, or antibodies, or other means and methods whereby peptides, polypeptides, or variants thereof cause to come together.

The term, "immunogenicity" as used herein is the degree to which a substance induces an immune response; whereas, the term "antigenicity" is used to describe the capacity to induce an immune response.

The term "impart," including grammatical variations thereof, as used herein means to give or convey.

The term "promote," including grammatical variations thereof, as used herein means to help bring about.

The term "resistance," including grammatical variations thereof, as used herein means to retard or oppose a particular effect (e.g., oppose attachment of plasma factors which foul tissue interfacing devices).

The term "sterilize," including grammatical variations thereof, as used herein means to make substantially free of viable microbes.

As used herein, "drug" is any therapeutic compound or molecule including but not limited to nucleic acids, small molecules, polypeptide or peptide, etc. The peptide may be any medically or diagnostically useful peptide or protein of small to medium size (i.e., up to about 75kDa). The mechanisms of improved polypeptide absorption are described in U.S. Pat. No. 5,661,130 to Meezan et al., the reference of which is hereby incorporated in its entirety. The present invention can be mixed with all such peptides, although the degree to which the peptides benefits are improved may vary according to the molecular weight and the physical and chemical properties of the peptide, and the particular surfactant used. Examples of polypeptides include antibodies, such as monoclonal antibodies, insulin like growth factor-I (IGF-I) or Somatomedin-C), insulin, calcitonin, leptin, hGH, human parathyroid hormone (PTH) or active fragments thereof, such as but not limited to PTH 1-31 (OSTABOLINO C™), PTH 1-34 and PTH 3-34, melatonin, GLP-1 or Glucagon-like peptide-1, GiP, OB-3 peptide, pituitary adenylate cyclase neuropeptide—activating polypeptide (PACAP), GM-1 ganglioside, nerve growth factor (NGF), D-(tryp6)-LHRH, nafarelin, FGF, VEGF, VEGF antagonists, Leuprolide, interferon-alpha, interferon-beta, interferon-gamma, low molecular weight heparin, PYY, LHRH, LH, GDNF, G-CSF, Ghrelin antagonists, Ghrelin, KGF, IMITREX™, Integrelin, Nesiritide, SANDOSTATIN™, cetrorelix acetate, ganirelix acetate, bivalirudin, zafirlukast, Exanitide, pramlintide acetate, vasopressin, desmopressin, glucagon, ACTH, GHRH and analogs, oxytocin, corticotropin releasing hormone, TRHrh, atrial natriuretic peptide, thyroxine releasing hormone, FSH, prolactin, Tobramycin, Triptorelin, Goserelin, FUZEON™, HEMATIDE™, Buserelin, Octreotide, Gonadorelin, Felypressin, Deslorelin, Vasopressin, 8-L-Arg, Eptifibatide, GM-CSF, EPO, Interleukin-11, Endostatin, Angiostatin, N-acetyl oxyntomodulin 30-37, Oxyntomodulin, Ularitide, Xerecept, Apo A-IV, rNAPc2, Secretin, Thymopentin, Neuromedin U, Neurotensin, Thrombospondin-1 inhibitors, FGF-18, FGF-20, FGF-21, Elcatonin Acetate, Antide Acetate, Dynorphin A (1-13) Acetate, Sincalide, Thymopentin Acetate, Thymosin alpha1 acetate (Thymalfasin), Fertirelin Acetate, CRF Acetate, CRF (ovine), Hisrelin, Thymalfasin, Ecallantide, Oxycortin, Urocortin, ARIXTRA™, Spiegelmer nucleotide aptamers, CGRP (calcitonin gene related protein), Urocortin, Amylin, IL-21, melanotan, valpreotide, ACV-1 neuropathic pain peptide, gastrin, gastrin releasing peptide (GRP), gastrin releasing peptide-like peptides, or epidermal growth factor. Also, see Table I.

In one aspect, antibodies are included as proteins in the compositions and methods of the invention, including functional fragments thereof. "Antibodies" as used herein includes polyclonal and monoclonal antibodies, chimeric, single chain, and humanized antibodies, as well as Fab fragments, including the products of an Fab or other immuno globulin expression library. Antibodies which consists essentially of pooled monoclonal antibodies with different epitopic specificities, as well as distinct monoclonal antibody preparations are provided. Monoclonal antibodies are made by methods well known to those skilled in the art. The term antibody as used in this invention is meant to include intact molecules as well as fragments thereof, such as Fab and F(ab')$_2$, Fv and SCA fragments which are capable of binding an epitopic determinant on a protein of interest. An Fab fragment consists of a mono-valent antigen-binding fragment of an antibody molecule, and can be produced by digestion of a whole antibody molecule with the enzyme papain, to yield a fragment consisting of an intact light chain and a portion of a heavy chain. An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner. An (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds. An Fv fragment is defined as a genetically engineered fragment containing the variable region of a light chain and the variable region of a heavy chain expressed as two chains. (5) A single chain antibody ("SCA") is a genetically engineered single chain molecule containing the variable region of a light chain and the variable region of a heavy chain, linked by a suitable, flexible polypeptide linker.

As used herein, a "monoclonal antibody" may be from any origin, such as mouse or human, including a chimeric antibody thereof. Additionally, the antibody may be humanized.

Examples of monoclonal antibodies (as named by the World Health Organization in International Nonproprietary Names (INN) for Biological and Biotechnological Substances publications; the number corresponding to the INN List including the antibody) include those of mouse origin including: abagovomab (95), afelimomab (80), altumomab (80), anatumomab mafenatox, (86) arcitumomab (74), bectumomab (81), besilesomab (92), bicromab (66), capromab (80), detumomab (80), dorlimomab aritox (66), edobacomab (80), edrecolomab (74), elsilimomab (89), enlimomab (80), enlimomab pegol (77), epitumomab (82), epitumomab cituxetan (89), faralimomab (81), gavilimomab (84), ibritumomab tiuxetan (86), igovomab (86), imciromab (66), inolimomab (80), lemalesomab (86), maslimomab (66), minretumomab (80), mitumomab (82), nacolomab tafenatox (80), nerelimornab (81), odulimomab (81), oregovomab (86), satumomab (81), sulesomab (86), taplitumomab paptox (84), technetium ($^{99m}$Tc) fanolesomab (86), technetium ($^{99m}$Tc) nofetumomab merpentan (81), technetium, ($^{99m}$Tc) pintumomab (86), telimomab aritox (66), tositumomab (80), vepalimomab (80), zolimomab aritox (80); those of human origin including: adalimumab (85), adecatumumab (90), atorolimumab (80), belimumab (89), bertilimumab (88), denosumab (94), efungumab (95), exbivirumab (91), golimumab (91), ipilimumab (94), iratumumab (94), lerdelimumab (86), lexatumumab (95), libivirumab (91), mapatumumab (93), metelimumab (88), morolimumab (79), nebacumab (66), ofatumumab (93), panitumumab (91), pritumumab (89), raxibacumab (92), regavirumab (80), sevirumab (66), stamulumab (95), ticilimumab (95), tuvirumab (66), votumumab (80), zalutumumab (93), zanolimumab (92), ziralimumab (84); those of chimeric origin including: abciximab (80), basiliximab (81), bavituximab (95), cetuximab (82), clenoliximab (77), ecromeximab (87), galiximab (89), infliximab (77), keliximab (81), lumiliximab (90), pagibaximab (93), priliximab (80), rituximab (77), teneliximab (87), vapaliximab (87), volociximab (93); and those of humanized origin including: alemtuzumab (83), apolizumab (87), aselizumab (88), bapineuzumab (93), bevacizumab (86), bivatuzumab (86), cantuzumab mertansine (89), cedelizumab (81), certolizumab pegol (90), daclizumab (78), eculizumab (87), efalizumab (85), epratuzumab (82), erlizumab (84), felvizumab (77), fontolizumab (87), gemtuzumab (83), inotuzumab ozogamicin (92), labetuzumab (85), lintuzumab (86), matuzumab (88), mepolizumab (81), motavizumab (95), natalizumab (79), nimotuzumab (94), ocrelizumab (95), omalizumab (84), palivizumab (79), pascolizumab (87), pertuzumab (89), pexelizumab (86), ranibizumab (90), reslizumab (85), rovelizumab (81), ruplizumab (83), sibrotuzumab (86), siplizumab (87), sontuzumab (94), tadocizumab (94), talizumab (89), tefibazumab (92), tocilizumab (90), toralizumab (87), trastuzumab (78), tucotuzumab celmoleukin (95), urtoxazumab (90), visilizumab (84), yttrium $^{90}$Y tacatuzumab tetraxetan (93).

As used herein, a "therapeutic composition" can comprise an admixture with an aqueous or organic carrier or excipient, and can be compounded, for example, with the usual non toxic, pharmaceutically acceptable carriers for tablets, pellets, capsules, lyophilizates, suppositories, solutions, emulsions, suspensions, or other form suitable for use. The carriers, in addition to those disclosed above, can include alginate, collagen, glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semi-solid, or liquid form. In addition, auxiliary stabilizing, thickening or coloring agents can be used, for example a stabilizing dry agent such as triulose.

As used herein, the term "therapeutic targets" may thus be defined as those analytes which are capable of exerting a modulating force, wherein "modulation" is defined as an alteration in function inclusive of activity, synthesis, production, and circulating levels. Thus, modulation effects the level or physiological activity of at least one particular disease related biopolymer marker or any compound or biomolecule whose presence, level or activity is linked either directly or indirectly, to an alteration of the presence, level, activity or generic function of the biopolymer marker, and may include pharmaceutical agents, biomolecules that bind to the biopolymer markers, or biomolecules or complexes to which the biopolymer markers bind. The binding of the biopolymer markers and the therapeutic moiety may result in activation (agonist), inhibition (antagonist), or an increase or decrease in activity or production (modulator) of the biopolymer markers or the bound moiety. Examples of such therapeutic moieties include, but are not limited to, antibodies, oligonucleotides, proteins (e.g., receptors), RNA, DNA, enzymes, peptides or small molecules. With regard to immunotherapeutic moieties, such a moiety may be defined as an effective analog for a major epitope peptide which has the ability to reduce the pathogenicity of key lymphocytes which are specific for the native epitope. An analog is defined as having structural similarity but not identity in peptide sequencing able to be recognized by T-cells spontaneously arising and targeting the endogenous self epitope. A critical function of this analog is an altered T-cell activation which leads to T-cell anergy or death.

As used herein, a "pharmaceutically acceptable carrier" or "therapeutic effective carrier" is aqueous or non aqueous (solid), for example alcoholic or oleaginous, or a mixture thereof, and can contain a surfactant, emollient, lubricant, stabilizer, dye, perfume, preservative, acid or base for adjustment of pH, a solvent, emulsifier, gelling agent, moisturizer, stabilizer, wetting agent, time release agent, humectant, or other component commonly included in a particular form of pharmaceutical composition. Pharmaceutically acceptable carriers are well known in the art and include, for example, aqueous solutions such as water or physiologically buffered saline or other solvents or vehicles such as glycols, glycerol, and oils such as olive oil or injectable organic esters. A pharmaceutically acceptable carrier can contain physiologically acceptable compounds that act, for example, to stabilize or to increase the absorption of specific inhibitor, for example, carbohydrates, such as glucose, sucrose or dextrans, antioxidants, such as ascorbic acid or glutathione, chelating agents, low molecular weight proteins or other stabilizers or excipients.

The pharmaceutical compositions can also contain other pharmaceutically acceptable auxiliary substances as required to approximate physiological conditions, such "substances" include, but are not limited to, pH adjusting and buffering agents, tonicity adjusting agents and the like, for example, sodium acetate, sodium lactate, sodium chloride, potassium chloride, calcium chloride, etc. Additionally, the peptide, polypeptide or variant thereof suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, are suitable.

As used herein, a "surfactant" is a surface active agent which is agents that modify interfacial tension of water. Typically, surfactants have one lipophilic and one hydrophilic group in the molecule. Broadly, the group includes soaps, detergents, emulsifiers, dispersing and wetting agents, and several groups of antiseptics. More specifically, surfactants include stearyltriethanolamine, sodium lauryl sulfate, sodium taurocholate, laurylaminopropionic acid, lecithin, benzalkonium chloride, benzethonium chloride and glycerin monostearate; and hydrophilic polymers such as polyvinyl alcohol, polyvinylpyrrolidone, carboxymethylcellulose sodium, methylcellulose, hydroxymethylcellulose, hydroxyethylcellulose and hydroxypropylcellulose.

As used herein, "alkylglycoside" refers to any sugar joined by a linkage to any hydrophobic alkyl, as is known in the art. The hydrophobic alkyl can be chosen of any desired size, depending on the hydrophobicity desired and the hydrophilicity of the saccharide moiety. In one aspect, the range of alkyl chains is from 9 to 24 carbon atoms; and further the range is from 10 to 14 carbon atoms.

As used herein, "Critical Micelle Concentration" or "CMC" is the concentration of an amphiphilic component (alkylglycoside) in solution at which the formation of micelles (spherical micelles, round rods, lamellar structures etc.) in the solution is initiated.

As used herein, "saccharide" is inclusive of monosaccharides, oligosaccharides or polysaccharides in straight chain or ring forms. Oligosaccharides are saccharides having two or more monosaccharide residues.

As used herein, "sucrose esters" are sucrose esters of fatty acids. Sucrose esters can take many forms because of the eight hydroxyl groups in sucrose available for reaction and the many fatty acid groups, from acetate on up to larger, more bulky fats that can be reacted with sucrose. This flexibility means that many products and functionalities can be tailored, based on the fatty acid moiety used. Sucrose esters have food and non-food uses, especially as surfactants and emulsifiers, with growing applications in pharmaceuticals, cosmetics, detergents and food additives. They are biodegradable, non-toxic and mild to the skin.

As used herein, a "suitable" alkylglycoside means one that fulfills the limiting characteristics of the invention, i.e., that the alkylglycoside be nontoxic and nonionic, and that it reduces the immunogenicity or aggregation of a compound when it is administered with the compound via the ocular, nasal, nasolacrimal, sublingual, buccal, inhalation routes or by injection routes such as the subcutaneous, intramuscular, or intravenous routes. Suitable compounds can be determined using the methods set forth in the examples.

The terms peptide, polypeptide and protein may be used interchangeably herein, or a peptide, polypeptide or variant thereof. As used herein, the term "polypeptide" is interpreted to mean a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides. "Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well-known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, AD Pribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-link formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W.H. Freeman and Company, New York (1993) and Wold, F., Posttranslational Protein Modifications: Perspectives and Prospects, pgs. 1 12 in POSTTRANSLATIONAL COVALENT MODIFICATION OF PROTEINS, B. C. Johnson, Ed., Academic Press, New York (1983); Seifter et al., Meth. Enzymol. 182:626 646 (1990) and Rattan et al., Protein Synthesis Posttranslational Modifications and Aging, Ann. N.Y. Acad. Sci. 663: 48 62 (1992). Polypeptides may be branched or cyclic, with or without branching. Cyclic, branched and branched circular polypeptides may result from post-translational natural processes and may be made by entirely synthetic methods, as well.

As used herein, the term "agent" is interpreted to mean a chemical compound, a mixture of chemical compounds, a sample of undetermined composition, a combinatorial small molecule array, a biological macromolecule, a bacteriophage peptide display library, a bacteriophage antibody (e.g., scFv) display library, a polysome peptide display library, or an extract made from biological materials such as bacteria, plants, fungi, or animal cells or tissues. Suitable techniques involve selection of libraries of recombinant antibodies in phage or similar vectors. See, Huse et al. (1989) Science 246: 1275 1281; and Ward et al. (1989) Nature 341: 544 546. The protocol described by Huse is rendered more efficient in combination with phage display technology. See, e.g., Dower et al., WO 91/17271 and McCafferty et al., WO 92/01047.

As used herein, the term "isolated" is interpreted to mean altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

As used herein, the term "variant" is interpreted to mean a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

The term "surfactant" comes from shortening the phrase "surface active agent". In pharmaceutical applications, surfactants are useful in liquid pharmaceutical formulations in which they serve a number of purposes, acting as emulsifiers, solubilizers, and wetting agents. Emulsifiers stabilize the aqueous solutions of lipophilic or partially lipophilic substances. Solubilizers increase the solubility of components of pharmaceutical compositions increasing the concentration which can be achieved. A wetting agent is a chemical additive which reduces the surface tension of a fluid, inducing it to spread readily on a surface to which it is applied, thus causing even "wetting" of the surface with the fluids. Wetting agents provide a means for the liquid formulation to achieve intimate contact with the mucous membrane or other surface areas with which the pharmaceutical formulation comes in contact.

While the effects of surfactants may be beneficial with respect to the physical properties or performance of pharmaceutical preparations, they are frequently irritating to the skin and other tissues and in particular are irritating to mucosal membranes such as those found in the nose, mouth, eye, vagina, rectum, buccal or sublingual areas, etc. Additionally, many and indeed most surfactants denature proteins thus destroying their biological function. As a result, they are limited in their applications. Since surfactants exert their effects above the critical micelle concentration (CMC) surfactants with low CMC's are desirable so that they may be utilized with effectiveness at low concentrations or in small amounts in pharmaceutical formulations. Typical alkylglycosides of the present invention have the CMC's less than 1 mM in pure water or in aqueous solutions. Some CMC values for alkylglycosides are listed below:
CMCs of some alkylglycosides in water:
Octyl maltoside 19.5 mM
Decyl maltoside 1.8 mM
Dodecyl β-D-maltoside 0.17 mM Tridecyl maltoside 0.03 mM
Tetradecyl maltoside 0.01 mM
Sucrose dodecanoate 0.3 mM The surfactants of the invention can also include a saccharide. As use herein, a "saccharide" is inclusive of monosaccharides, oligosaccharides or polysaccharides in straight chain or ring forms, or a combination thereof to form a saccharide chain. Oligosaccharides are saccharides having two or more monosaccharide residues. The saccharide can be chosen, for example, from any currently commercially available saccharide species or can be synthesized. Some examples of the many possible saccharides to use include glucose, maltose, maltotriose, maltotetraose, sucrose and trehalose. Preferable saccharides include maltose, sucrose and glucose.

The surfactants of the invention can likewise consist of a sucrose ester. As used herein, "sucrose esters" are sucrose esters of fatty acids. Sucrose esters can take many forms because of the eight hydroxyl groups in sucrose available for reaction and the many fatty acid groups, from acetate on up to larger, more bulky fatty acids that can be reacted with sucrose. This flexibility means that many products and functionalities can be tailored, based on the fatty acid moiety used. Sucrose esters have food and non-food uses, especially as surfactants and emulsifiers, with growing applications in pharmaceuticals, cosmetics, detergents and food additives. They are biodegradable, non-toxic and mild to the skin.

While there are potentially many thousands of alkylglycosides which are synthetically accessible, the alkylglycosides dodecyl, tridecyl and tetradecyl maltoside and sucrose dodecanoate, tridecanoate, and tetradecanoate are particularly useful since they possess desirably low CMC's. Hence, the above examples are illustrative, but the list is not limited to that described herein. Derivatives of the above compounds which fit the criteria of the claims should also be considered when choosing a glycoside. All of the compounds can be screened for efficacy following the methods taught herein and in the examples.

In one embodiment of the invention, the present invention provides a composition which reduces, prevents, or lessens peptide or protein association or aggregation in the composition, for example, reduces peptide or protein self-association or self-aggregation, or reduces association or aggregation with other peptides or proteins when administered to the subject.

Self-Association at high protein concentration is problematic in therapeutic formulations. For example, self-association increases the viscosity of a concentrated monoclonal antibody in aqueous solution. Concentrated insulin preparations are inactivated by self aggregation. These self associating protein interactions, particularly at high protein concentration, reduce, modulate or obliterate biological activity of many therapeutics. Therapeutic proteins formulated at high concentrations for delivery by injection or other means can be physically unstable or become insoluble as a result of these protein interactions.

A main challenge of protein formulation is to develop manufacturable and stable dosage forms. Physical stability properties, critical for processing and handling, are often poorly characterized and difficult to predict. A variety of physical instability phenomena are encountered such as association, aggregation, crystallization and precipitation, as determined by protein interaction and solubility properties. This results in several manufacturing, stability, analytical, and delivery challenges.

Development of such formulations for protein drugs requiring high dosing (on the order of mg/kg) are required in many clinical situations. For example, using the SC route, approximately <1.5 mL is the allowable administration volume. This may require >100 mg/mL protein concentrations to achieve adequate dosing. Similar considerations exist in developing a high-concentration lyophilized formulation for monoclonal antibodies.

In general, higher protein concentrations permit smaller injection volume to be used which is very important for patient comfort, convenience, and compliance. Because injection is an uncomfortable mode of administration for many people, other means of administering peptide therapeutics have been sought. Certain peptide and protein therapeutics maybe administered, by example, by intranasal administration. An example is calcitonin which is administered in a nasal spray. However there is a limit to the volume that can be practically dispensed into the nose without significant amount draining out.

Typical formulation parameters include selection of optimum solution pH, buffer, and stabilizing excipients. Additionally, lyophilized cake reconstitution is important for lyophilized or powdered formulations. A further and significant problem comprises changes in viscosity of the protein formulation upon self association. Changes in viscosity can significantly alter delivery properties. This is perhaps most critical in spray (aerosol) delivery for intranasal, pulmonary, or oral cavity sprays. Furthermore, increased viscosity can make injection delivery by syringe or iv line more difficult or impossible.

Many peptide and protein molecules with useful therapeutic activity (hereafter called protein therapeutics) have been, and continued to be, discovered, therefore increasing the need for improved formulation technology. Examples include insulin, growth hormone, interferons, calcitonin, parathyroid hormone, and erythropoietin, among many others. Table I lists examples of peptide and protein therapeutics.

TABLE I

Examples of Peptide and Protein Therapeutics

| | | | |
|---|---|---|---|
| 1. | Insulin like growth factor-I (IGF-I or Somatomedin-C) | 2. | Insulin |
| 3. | Calcitonin | 4. | Leptin and metroleptin |
| 5. | hGH | 6. | Human parathyroid hormone (PTH) parathyroid hormone or active fragments thereof (i.e., PTH 1-31, PTH 1-34 and PTH 3-34) |
| 7. | Melatonin | 8. | GLP-1 or Glucagon-like peptide-1 |
| 9. | GiP | 10. | OB-3 peptide |
| 11. | Pituitary adenylate cyclase neuropeptide - activating polypeptide (PACAP) | 12. | GM-1 ganglioside |
| 13. | Nerve growth factor (NGF), | 14. | D-(tryp6)-LHRH |
| 15. | Nafarelin | 16. | FGF |
| 17. | VEGF | 18. | VEGF antagonists |
| 19. | Leuprolide | 20. | Interferon-alpha |
| 21. | Interferon-beta | 22. | Interferon-gamma |
| 23. | Low molecular weight heparin | 24. | PYY |
| 25. | LHRH | 26. | LH |
| 27. | GDNF | 28. | G-CSF |
| 29. | Ghrelin antagonists | 30. | Ghrelin |
| 31. | KGF | 32. | IMITREX ™ |
| 33. | Integrelin | 34. | Nesiritide |
| 35. | SANDOSTATIN ™ | 36. | PTH (1-34) |
| 37. | desmopressin acetate | 38. | cetrorelix acetate |
| 39. | ganirelix acetate | 40. | bivalirudin |
| 41. | zafirlukast | 42. | Exanitide |
| 43. | pramlintide acetate | 44. | Vasopressin |
| 45. | Desmopressin | 46. | Glucagon |
| 47. | ACTH | 48. | GHRH and analogs |

TABLE I-continued

Examples of Peptide and Protein Therapeutics

| | | | |
|---|---|---|---|
| 49. | Oxytocin | 50. | corticotropin releasing hormone |
| 51. | TRHrh | 52. | Atrial natriuretic peptide |
| 53. | Thyroxine releasing hormone | 54. | FSH |
| 55. | Prolactin | 56. | Tobramycin |
| 57. | Triptorelin | 58. | Goserelin |
| 59. | FUZEON ™ | 60. | HEMATIDE ™ |
| 61. | Buserelin | 62. | Octreotide |
| 63. | Gonadorelin | 64. | Felypressin |
| 65. | Deslorelin | 66. | Vasopressin, 8-L-Arg |
| 67. | Eptifibatide | 68. | GM-CSF |
| 69. | EPO | 70. | Interleukin-11 |
| 71. | Endostatin | 72. | Angiostatin |
| 73. | N-acetyl oxyntomodulin 30-37 | 74. | Oxyntomodulin |
| 75. | Ularitide | 76. | Xerecept |
| 77. | Apo A-IV | 78. | rNAPc2 |
| 79. | SECRETIN | 80. | Thymopentin |
| 81. | Neuromedin U | 82. | Neurotensin |
| 83. | Thrombospondin-1 inhibitors | 84. | FGF-18 |
| 85. | FGF-20 | 86. | FGF-21 |
| 87. | Elcatonin Acetate | 88. | Antide Acetate |
| 89. | Dynorphin A (1-13) Acetate | 90. | Sincalide |
| 91. | Thymopentin Acetate | 92. | Thymosin alpha1 acetate (Thymalfasin) |
| 93. | Fertirelin Acetate | 94. | CRF Acetate |
| 95. | CRF (ovine) | 96. | Hisrelin |
| 97. | Thymalfasin | 98. | Ecallantide |
| 99. | Oxycortin | 100. | Urocortin |
| 101. | Arixtra | 102. | Spiegelmer nucleotide aptamers |
| 103. | CGRP (calcitonin gene related protein) | 104. | Amylin |
| 105. | IL-21 | 106. | melanotan |
| 107. | valpreotide | 108. | ACV-1 neuropathic pain peptide |
| 109. | CTLA4-Ig fusion protein | | |

Many attempts to stabilize and maintain the integrity and physiological activity of proteins and peptides have been reported. Some attempts have produced stabilization against thermal denaturation and aggregation, particularly for insulin pump systems. Polymeric surfactants were studied by Thurow and Geisen (1984) and Chawla et al., (1985) used polyol-surfactants. The stabilization of insulin by these compounds was believed to be of a steric nature. Among other systems used are saccharides (Arakawa and Timasheff, 1982), osmolytes, such as amino acids (Arakawa and Timasheff, 1985), and water structure breakers, such as urea (Sato et al., 1983). These compounds exert their action by modulating the intramolecular hydrophobic interaction of the protein.

Hence, as used herein, the terms "association" or "aggregation" are used interchangeably. Protein association or aggregation is a common property of any polypeptide chain and the process can begin from at least a partially unfolded state. Peptide or protein aggregation can form insoluble intracellular complexes, for example, amyloid plaques in neurodegenerative disorders. Peptide or protein aggregation can occur between one type or sub-types of class or family of peptides or proteins or with another type or sub-type of a different class or family of peptides or proteins; the former is an example of peptide or protein "self-association" or "self-aggregation".

Because many protein therapeutics undergo aggregation at high concentration, it was desirable that a means be discovered to prevent self association for the reasons mentioned above. Agents useful in preventing self-aggregation of proteins at high concentrations or controlling viscosity must be essentially non-toxic and metabolized to non-toxic products. Ideally, the agents should be physiologically occurring substances or should metabolize to physiologically occurring molecules and should not be subject to accumulation in the patients' tissues or organs.

Dodecyl maltoside has been demonstrated to prevent self-association of insulin and thus prevent inactivation of biological activity. However, various peptides, polypeptides, or proteins are encompassed in the present invention. Humanin peptides, a promising new class of therapeutics, also aggregate thus limiting their biological activity, and investigators have had to resort to modifying the protein sequence to reduce such aggregation.

Native human amylin, also known as Islet Amyloid Polypeptide (IAPP), is a 37 amino acid peptide hormone secreted by pancreatic β-cells at the same time as insulin (in a roughly 100:1 ratio). Amylin is a member of a family of related peptides which include CGRP and calcitonin. Amylin is primarily synthesized in pancreatic beta cells and is secreted in response to nutrient stimuli such as glucose and arginine. Amylin is commonly found in pancreatic islets of patients suffering diabetes mellitus type II, or harboring an insulinoma. It has been isolated, purified and chemically characterized as the major component of amyloid deposits in the islets of pancreases of human Type II diabetics.

The physiological role of amylin in fuel metabolism and it's link to disorders such as diabetes and obesity is well known. For example, amylin is known to reduce glycogen-synthase activity, promote conversion of glycogen phosphorylase from the inactive b form to the active a form, promote net loss of glycogen (in the presence or absence of insulin), increases glucose-6-phosphate levels, and increase lactate output. Additionally, amylin has been shown to have an effect on the secretion of insulin, stimulate of a sharp rise in plasma lactate followed by a rise in plasma glucose, slow gastric emptying, act as a vasodialator, and suppress food intake. Further discussion of the physiological role of amylin and use of amylin, and synthetic analogs thereof, for the treatment of diabetes and obesity is provided, for example, in U.S. Pat. Nos. 6,417,164; 6,143,718; 6,110,707; 5,814,600; 5,641,744; 5,424,394; 5,367,052; 5,312,008; 5,175,145; 5,124,314; and 5,112,945; incorporated herein by reference.

The amylin molecule has two important post-translational modifications: the C-terminus is amidated, and the cysteines in positions 2 and 7 are cross-linked through a disulfide bridge to form an N-terminal loop. In vitro, the human form of amylin aggregates in solution due to fibril formation. Within the fibrillization reaction, the early prefibrillar structures are extremely toxic to insuloma cells cultures. As a result of the tendency of amylin to form fibrils in solution, the native form of amylin exhibits low solubility and stability characteristics, thereby decreasing the protein's suitability and effective use as a therapeutic.

Various modified synthetic analogs of human-amylin peptides have been made in an attempt to increase the solubility and stability characteristics of the peptides that result for fibrillization. For example, pramlintide acetate, a known diabetes therapeutic, is a synthetic analog of human-amylin substituted with the following amino acids at the specified positions: $Pro^{25}$ $Pro^{28}$ $Pro^{29}$. However, such synthetic analogs of modified human-amylin peptides are less effective and/or potent than native human-amylin. Additionally, it is expected that synthetic analogs of native proteins exhibit increased immunogenicity as compared to the native protein resulting in unwanted immunogenic side-effects.

Accordingly, a composition including the native form of amylin admixed with a stabilizing agent of the present invention, capable of preventing fibril formation of amylin in solution, results in a therapeutic composition exhibiting increased stability, reduced aggregation and reduced immunogenicity, as compared to previously attempted compositions. Accordingly, in one aspect, the present invention provides a pharmaceutical composition for increasing the stability, reducing aggregation or reducing immunogenicity of amylin, including amylin and a stabilizing agent, such as an alkylglycoside.

Other peptides useful in the treatment of diabetes mellitus are gastrin, gastrin releasing peptide (GRP), and gastrin releasing peptide-like proteins. Gastrin is a linear peptide produced by G cells of the duodenum and in the pyloric antrum of the stomach. It is secreted into the bloodstream. Gastrin is found primarily in three forms known as gastrin-34, gastrin-17, gastrin-14. Gastrin releasing peptide (GRP) is a member of the bombesin-like family of gastrin-releasing peptides. It is a 27 amino acid peptide first isolated from porcine gut. One biological role of GRP is stimulation of the release of gastrin from the stomach mucosa. Additional peptides having gastrin releasing peptide-like activity, are also known as disclosed, for example, in U.S. Pat. No. 4,613,586, incorporated herein by reference. Gastrin and analogs thereof, alone or in combination with GLP-1 analogs or EGF analogs, have been shown effective in patients with type 2 diabetes in reducing blood glucose control parameters, including haemoglobinA 1 C, for up to 6 months post treatment.

Accordingly, one aspect of the present invention includes a method for the treatment of diabetes by administering to a subject a composition exhibiting increased stability, reduced aggregation and reduced immunogenicity including gastrin, gastrin releasing peptide (GRP), and gastrin releasing peptide-like proteins alone or in combination with EGF and/or GLP-1 stabilized by an alkylglycoside.

Peptide T, and in particular its longer half-life analog D-Ala-Peptide T-amide (DAPTA), a very promising therapeutic for treatment of HIV infection which has been shown to eliminate residual infectious virus in the monocyte reservoir upon repeated administration, is subject to very rapid aggregation and inactivation, thus limiting the usefulness (Ruff et al. 2001; Ruff et al. 2003; Polianova et al., 2003).

The Peptide T analog referred to as DAPTA is an octapeptide related to the V2 region of HIV-1 gp120 and has been shown to be a non-toxic, CCR5 HIV entry inhibitor that reduces plasma and persistently infected, treatment resistant macrophage reservoirs for at least six months. The chemokine receptor CCR5 plays a crucial role in transmission of HIV isolates that predominate in the early and middle stages of infection as well as those that populate the brain and cause neuro-AIDS. CCR5 is therefore an attractive therapeutic target for design of entry inhibitors.

Peptide T has a number of analogs. The most clinically useful is DAPTA which is D-ala$^1$-Peptide T-amide. However, other useful Peptide T analogs include: D-ala$^1$-Peptide T (lacks an amide at the C-terminus); D-ala$^1$Thr$^8$-Peptide T amide; Vasoactive Intestinal peptide (VIP); Thr-Thr-Ser-Tyr-Thr (SEQ ID NO:1; an active pentamer); and RANTES antagonists. RANTES is an octapeptide (Brain Research (1999) 838:27-36), and an acronym for Regulated on Activation, Normal T Expressed and Secreted. It is also known as CCL5. RANTES is a cytokine that is a member of the interleukin-8 superfamily of cytokines. RANTES is a protein. It is a selective attractant for memory T lymphocytes and monocytes. It binds to CCR5, a coreceptor of HIV. Blocking RANTES prevents HIV entry into cells.

Despite significant therapeutic successes major obstacles to a cure remain. The inability of current antiviral drugs to flush cellular viral reservoirs causes re-infection in the body. Toxicities, viral resistance, complicated regimens, and high cost greatly limit the effectiveness of current therapies in the battle against global AIDS.

DAPTA has been clinically studied for almost 20 years and shown to be completely non-toxic, effective in Phase I and placebo controlled phase II NIH trials. This octapeptide is easy to manufacture and effective at very low doses so that costs will be very low (less than $500 per year). It may be administered as a convenient nasal spray. The drug, which has been tested with other antiviral regimens, is expected to have synergistic treatment benefits without cross-tolerance and has been demonstrated to be free of viral resistance for at least six months.

DAPTA has recently been proven to act as a receptor blocking entry inhibitor at CCR5 receptors (Polionova et al., 2005), a mechanism of action shown to be a highly desirable one for an HIV-1 therapy (Moore, 2006). The HIV envelop (gp-120) derived Peptide T sequence was deduced late in 1985 in a computer assisted database search for the part of the virus which attaches to its receptor. Sophisticated knowledge of peptide receptor pharmacology allowed the inventors, then at the NIH, to create a small long-lasting peptide therapeutic that blocked viral binding and infection (Pert et al PNAS 1986).

In 1987, the report that DAPTA potently (10 pM) blocks envelop (gp120) binding and inhibits viral infectivity was met with vociferous objections from the American HIV virological community which had failed to find a gp-120 receptor active peptide sequence after an extensive search. Objections, which were based on the failure to replicate DAPTA's antiviral effects in vitro, greatly diminished interest in clinical testing through the NIH/NIAD despite a report from Sweden (Wetterberg, et al., 1987) of dramatic improvements in four near terminal men with AIDS. The scientific controversy was resolved in 2001 with the demonstration (Ruff et al., 2001) that DAPTA targets CCR5, not CxCR4 chemokine co-receptors which prevailed in the Gallo lab-adapted strain in general use in 1987 and which is not representative of the HIV isolates that predominate in early HIV infection. The first report of DAPTA's potent antiviral activity, 9 years before Peptide T chemokine co-receptors were known, had used Ruscetti's more physiological primary isolate now realized to be a CCR5-using virus.

Between 1987 and 1990, Phase I clinical studies conducted by the NIMH with some private funds showed a complete lack of toxicity, improvements in peripheral neuropathies, and apparent positive benefits in NeuroAIDS, the focus of the NIMH. A phase II placebo-controlled NIMH trial conducted between 1990-1995 involved three sites, and 240 patients. This $11M effort showed that DAPTA had significant clinical benefits versus placebo for more cognitively impaired patients and a CD4 cell increase fell just short of statistical significance. A recent blind NIMH analysis of virus levels in stored frozen plasma from this trial recently revealed a significant ($p<0.04$) treatment effect.

In a trial of eleven persons (Polionova, et al., 2003) progressively less actual virus could be isolated from white blood cells and the treatment-resistant persistently infected monocyte reservoir was greatly reduced or flushed to undetectable levels in all patients. In a small study, reversal of growth hormone secretion suppression has been reported in children. In the last few years, analyses of the properties of formulated peptide and detailed structural studies (MacPhee, unpublished) have revealed the very strong tendency of DAPTA to aggregate upon storage resulting in the loss of both bioavailability and antiviral activity. It is now clear that this property of DAPTA has sometimes led to suboptimal clinical results (Simpson et al., 1996) and even to falsely negative in vitro results. DAPTA has also been shown to resolve psoriatic lesions in an inflammatory skin disease (Raychaudhuria et al., 1999).

Still, other reports describe the tendency of DAPTA to aggregate and form fibrils. For example, peptide T solutions have been reported to thicken and "gel", potential loss of activity and/or the ability to be transported through the mucous membrane, e.g., the nasal epithelium, was a consideration. Removing sodium chloride from the formulation and lowering the concentration to 5 mgs per mL appeared to solve the problem. However, even at only 1 mg/mL, spectropolarimetric analysis at room temperature revealed a shift from a large peak at the more dilute 0.1 mg/ml of 205.4 nm to a large peak at 237.2 nm, indicating that the Peptide T was interacting with itself at higher concentrations in aggregation steps which would lead to gelation. Electron microscopy confirmed that Peptide T formed fibrils, and to our best knowledge Peptide T forms fibrils more readily than any other small peptide yet described (FIG. 1). In the present invention it has been discovered that this aggregation phenomenon results in loss of biological activity. Furthermore this tendency to aggregate or form fibrils not only varies from manufacturer to manufacturer but also varies unpredictably from batch to batch as illustrated in the examples that follow.

Chronic formation is concentration and temperature dependent, with fibrils forming most rapidly at refrigerator temperatures and concentrations at and above 1 mg/mL. For example, over many weeks of storage in the refrigerator, even 0.1 mg/mL peptide T solution gradually and progressively lost substantially all ability to block HIV infection, as shown in the Examples below. Also, when a formulation of peptide T is stored for many months, e.g., in the refrigerator (about 4° C.), it showed a 10-fold diminished ability to enter the plasma upon administering via intra-nasal metered spray. The effects of fibrils were considered so relevant and important that the Advanced ImmuniTy, Inc. (AITI), halted the clinical trials administering peptide T to treat psoriasis.

Chronic neuroinflammation plays a prominent role in the progression of Alzheimer's disease. Reactive microglia and astrocytes are observed within the hippocampus during the early stages of the disease. Epidemiological findings suggest that anti-inflammatory therapies may slow the onset of Alzheimer's disease. Chemokine receptor 5 (CCR5) up-regulation may influence the recruitment and accumulation of glia near senile plaques; activated microglia express CCR5 and reactive astrocytes express chemokines. Rosi, Pert and Ruff have previously shown that neuroinflammation induced by chronic infusion of lipopolysaccharide into the 4th ventricle reproduces many of the behavioral, neurochemical, electrophysiological and neuropathological changes associated with Alzheimer's disease (Pert et al. 2005).

In another embodiment, the present invention provides compositions having a peptide or protein drug and a surfactant having a CMC of less than about 1 mM, and preferably less than about 0.5 mM, that reduces or prevents aggregation while not denaturing the peptide or protein thus reducing or eliminating immunogenicity of the peptide or protein therapeutic upon administration to a vertebrate, and which is not irritating but is nontoxic, either at the site of application or systemically. Such a surfactant-peptide/protein drug composition is provided herein.

In one embodiment, the present invention is based on the discovery that therapeutic compositions comprising of least one self-associating peptide or protein drug and at least one surfactant, wherein the surfactant is further comprised of at least one alkylglycoside, form stable, non-irritating formulations in which the aggregation of the self-aggregating protein or peptide is greatly reduced or eliminated, resulting in one or more benefits such as reduced or eliminated immunogenicity, reduced or eliminated loss of biological activity resulting from aggregation, a longer shelf life, or reduced cold chain requirements as a result of reduction or elimination of inactivation upon spontaneous aggregation.

As used herein, "nontoxic" means that the alkylglycoside molecule has a sufficiently low toxicity to be suitable for human administration and consumption. Preferred alkylglycosides are nonirritating to the tissues to which they are applied. Any alkylglycoside should be of minimal or no toxicity to the tissues, such as not to cause damage to the cell in vivo. It is significant that the determination of toxicity be conducted in vivo, rather than in vitro. Much confusion and misinformation concerning the relative toxicity of excipients exists. This is largely the result of the currently unwarranted and uncritical reliance upon in vitro testing methods. For example, recent studies directly comparing in vitro and in vivo results have clearly demonstrated a lack of correlation between in vitro and in vivo tests in predicting nasal irritation or toxicity. A well studied example is benzalkonium chloride (BAC). BAC has been used in nasal and ophthalmic products since 1935 at concentrations up to 0.1%. However, over the past few years there have been conflicting reports of damage to human epithelia and exacerbation of rhinitis associated with products incorporating BAC.

In an extensive review and thorough analysis of the scientific publications on this subject, Marple et al (Marple 2004) concluded that the current data indicate that any concerns raised were limited to results from in vitro experiments. In direct contrast, analysis of the in vivo data suggested that even prolonged use of topical formulations containing BAC caused no significant damage to the nasal mucosa. The data analyzed were taken from 14 in vivo studies in which changes in the function and ultrastructure of nasal cilia were determined by various types of microscopy including light microscopy, transmission electron microscopy, scanning electron microscopy, and inverted phase microscopy (Ainge 1994; Berg 1995; Braat 1995; Graf 1999; Holm 1998; Kiossek 2001; McMahon 1997). Direct mucociliary clearance was evaluated via measurement of indigo carmine saccharine transport time or saccharine clearance time and exacerbation of rhinitis was determined by changes in nasal epithelia thickness. Likewise, in a well controlled double blind nasal biopsy study, 22 patients with perennial allergic rhinitis receiving fluticasone propionate aqueous nasal spray containing either BAC, BAC plus placebo, or BAC alone for a six week period were studied (Braat 1995). There were no statistical differences between indigocarmine saccharine transport time and the number of ciliated cells present for each group, and scanning and transmission electron microscopy examination of the biopsied tissues showed no effects of BAC.

In another recent study examining nasal irritation caused by benzalkonium chloride at 0.02%, saccharine transport time, anterior rhinomanometry, determination of nasal secretions, orienting smell test, and anterior rhinoscopy showed no discernible negative effects whatsoever (Lange 2004).

In a similar study by McMahon et al (McMahon 1997), conducted with 65 normal volunteers over a two week period, no significant difference was found between subjects receiving nasal spray with or without BAC at 0.02% twice a day on a double-blind basis. Symptoms scored included acoustic rhinometry, saccharine clearance time, and ciliary beat frequency. BAC caused a slight prolongation of mucosal ciliary clearance after application, but reportedly had no detectable effect on the nasal mucosal function after two weeks of continual regular use.

Another study which highlights the lack of correlation of in vitro testing with in vivo experience in humans (Riechelmann 2004) and one which also offers a simple and plausible explanation of the lack of correlation, the effect of the BAC on isolated nasal cilia taken from 15 human donors was examined. In in vitro testing, BAC was seen to be ciliotoxic. However, once again, in in vivo tests BAC did not alter saccharine transport time or indicators of proinflammatory effects, namely myeloperoxidase, and secretion of IL-6 and Substance P. The authors conclude that since no BAC-related proinflammatory effects are observed that any ciliotoxic effect of BAC is probably neutralized by components of secretions. This should not be too surprising since this is essentially the function of the nasal secretions in the mucociliary clearance process.

Thus it is clear that in vitro prediction of toxicity does not correlate with actual in vivo experience in human subjects, and in vivo results are preferred in making such assessments.

Toxicity for any given alkylglycoside may vary with the concentration of alkylglycoside used. It is also beneficial if the alkylglycoside chosen is metabolized or eliminated by the body and if this metabolism or elimination is done in a manner that will not be harmfully toxic.

In another embodiment of the invention, fluorinated organic solvents, polypeptide or variant thereof, or the peptide, polypeptide or variant thereof is admixed with a fluorinated organic solvent. The fluorinated organic solvent 2,2,2-trifluoroethanol (TFE) induces formation helical content within peptide chains. For example TFE induces up to 48% helical content within residues 1-20 of the peptide actin (Sonnichsen et al., 1992). Yet, another fluorinated organic solvent that induces structural changes within peptide chains is 1,1,1,3,3,3-hexafluoro-2-propanol (HFIP).

Particular properties of TFE or HFIP make them ideal solvent for peptides, polypeptides or variants thereof.

TFE and HFIP are commercially available in high purity. Thus, in another aspect of the invention, peptides, polypeptides and/or variants thereof can be admixed with TFE or HFIP alone, or with any of the alkyl glycosides described herein.

Many alkylglycosides can be synthesized by known procedures, i.e., chemically, as described, e.g., in Rosevear et al., Biochemistry 19:4108-4115 (1980) or Koeltzow and Urfer, J. Am. Oil Chem. Soc., 61:1651-1655 (1984), U.S. Pat. No. 3,219,656 and U.S. Pat. No. 3,839,318 or enzymatically, as described, e.g., in Li et al., J. Biol. Chem., 266:10723-10726 (1991) or Gopalan et al., J. Biol. Chem. 267:9629-9638 (1992).

The linkage between the hydrophobic alkyl and the hydrophilic saccharide can include, among other possibilities, a glycosidic, thioglycosidic (Horton), amide (Carbohydrates as Organic Raw Materials, F. W. Lichtenthaler ed., VCH Publishers, New York, 1991), ureide (Austrian Pat. 386,414 (1988); Chem. Abstr. 110:137536p (1989); see Gruber, H. and Greber, G., "Reactive Sucrose Derivatives" in Carbohydrates as Organic Raw Materials, pp. 95-116) or ester linkage (Sugar Esters: Preparation and Application, J. C. Colbert ed., (Noyes Data Corp., New Jersey), (1974)).

Examples from which useful alkylglycosides can be chosen for the therapeutic composition include: alkylglycosides, such as octyl-, nonyl-, decyl-, undecyl-, dodecyl-, tridecyl-, tetradecyl, pentadecyl-, hexadecyl-, heptadecyl-, and octadecyl-D-maltoside, -glucoside or -sucroside (i.e., sucrose ester) (synthesized according to Koeltzow and Urfer; Anatrace Inc., Maumee, Ohio; Calbiochem, San Diego, Calif.; Fluka Chemie, Switzerland); alkyl thiomaltosides, such as heptyl, octyl, dodecyl-, tridecyl-, and tetradecyl-β-D-thiomaltoside (synthesized according to Defaye, J. and Pederson, C., "Hydrogen Fluoride, Solvent and Reagent for Carbohydrate Conversion Technology" in Carbohydrates as Organic Raw Materials, 247-265 (F. W. Lichtenthaler, ed.) VCH Publishers, New York (1991); Ferenci, T., J. Bacteriol., 144:7-11 (1980)); alkyl thioglucosides, such as heptyl- or octyl 1-thio β- or β-D-glucopyranoside (Anatrace, Inc., Maumee, Ohio; see Saito, S, and Tsuchiya, T. Chem. Pharm. Bull. 33:503-508 (1985)); alkyl thiosucroses (synthesized according to, for example, Binder, T. P. and Robyt, J. F., Carbohydr. Res. 140:9-20 (1985)); alkyl maltotriosides (synthesized according to Koeltzow and Urfer); long chain aliphatic carbonic acid amides of sucrose amino-alkyl ethers; (synthesized according to Austrian Patent 382,381 (1987); Chem. Abstr., 108:114719 (1988) and Gruber and Greber pp. 95-116); derivatives of palatinose and isomaltamine linked by amide linkage to an alkyl chain (synthesized according to Kunz, M., "Sucrose-based Hydrophilic Building Blocks as Intermediates for the Synthesis of Surfactants and Polymers" in Carbohydrates as Organic Raw Materials, 127-153); derivatives of isomaltamine linked by urea to an alkyl chain (synthesized according to Kunz); long chain aliphatic carbonic acid ureides of sucrose amino-alkyl ethers (synthesized according to Gruber and Greber, pp. 95-116); and long chain aliphatic carbonic acid amides of sucrose amino-alkyl ethers (synthesized according to Austrian Patent 382,381 (1987), Chem. Abstr., 108:114719 (1988) and Gruber and Greber, pp. 95-116).

Some preferred glycosides include maltose, sucrose, and glucose linked by glycosidic or ester linkage to an alkyl chain of 9, 10, 12, 13 or 14 carbon atoms, e.g., nonyl-, decyl-, dodecyl- and tetradecyl sucroside, glucoside, and maltoside. These compositions are nontoxic, since they are degraded to an alcohol or fatty acid and an oligosaccharide, and amphipathic.

The above examples are illustrative of the types of alkylglycosides to be used in the methods claimed herein; the list is not exhaustive. Derivatives of the above compounds which fit the criteria of the claims should also be considered when choosing an alkylglycoside. All of the compounds can be screened for efficacy following the methods taught in the examples.

In sugar chemistry, an anomer is either of a pair of cyclic stereoisomers (designated α or β) of a sugar or glycoside, differing only in configuration at the hemiacetal (or hemiketal) carbon, also called the anomeric carbon or reducing carbon. If the structure is analogous to one with the hydroxyl group on the anomeric carbon in the axial position of glucose, then the sugar is an alpha anomer. If, however, that hydroxyl is equatorial, the sugar is a beta anomer. For example, α-D-glucopyranose and β-D-glucopyranose, the two cyclic forms of glucose, are anomers. Likewise, alkylglycosides occur as anomers. For example, dodecyl β-D-maltoside and dodecyl α-D-maltoside are two cyclic forms of dodecyl maltoside. The two different anomers are two distinct chemical structures, and thus have different physical and chemical properties. In one aspect of the invention, the alkylglycoside of the present invention is a β anomer. In another aspect, the alkylglycoside of the present invention is dodecyl β-D-maltoside.

Figure 7:
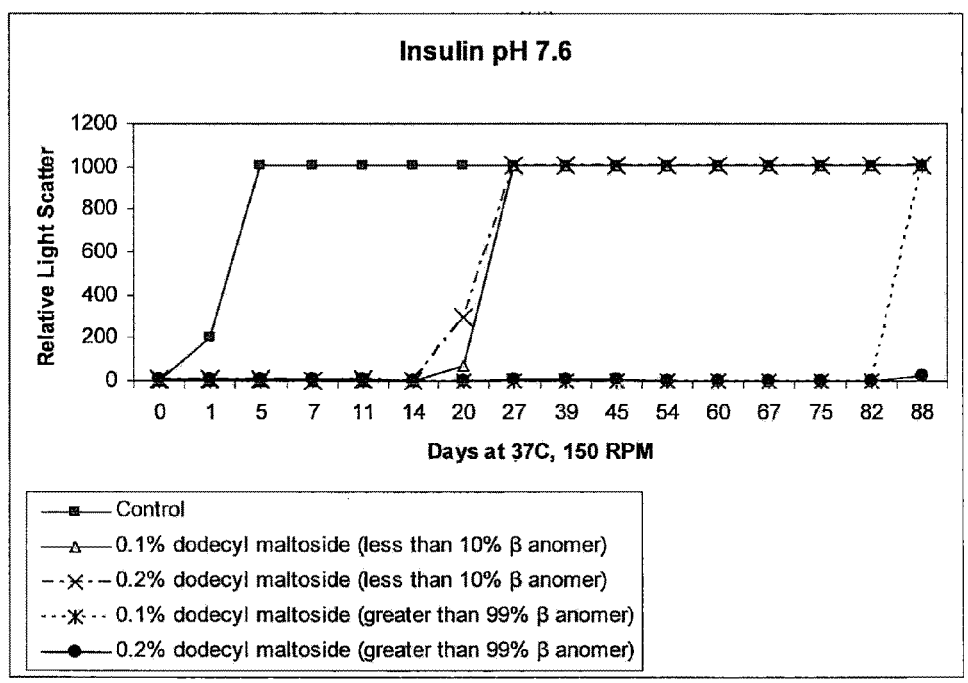
FIG. 7 is a graph showing light scatter readings for the polypeptide insulin at pH 7.6, admixed with 0.1% dodecyl maltoside containing less than 10% β anomer (Δ), 0.2% dodecyl maltoside including less than 10%β anomer (x), 0.1% dodecyl maltoside including greater than 99%β anomer (+), and 0.2% dodecyl maltoside including greater than 99% β anomer (●).
Figure 8:
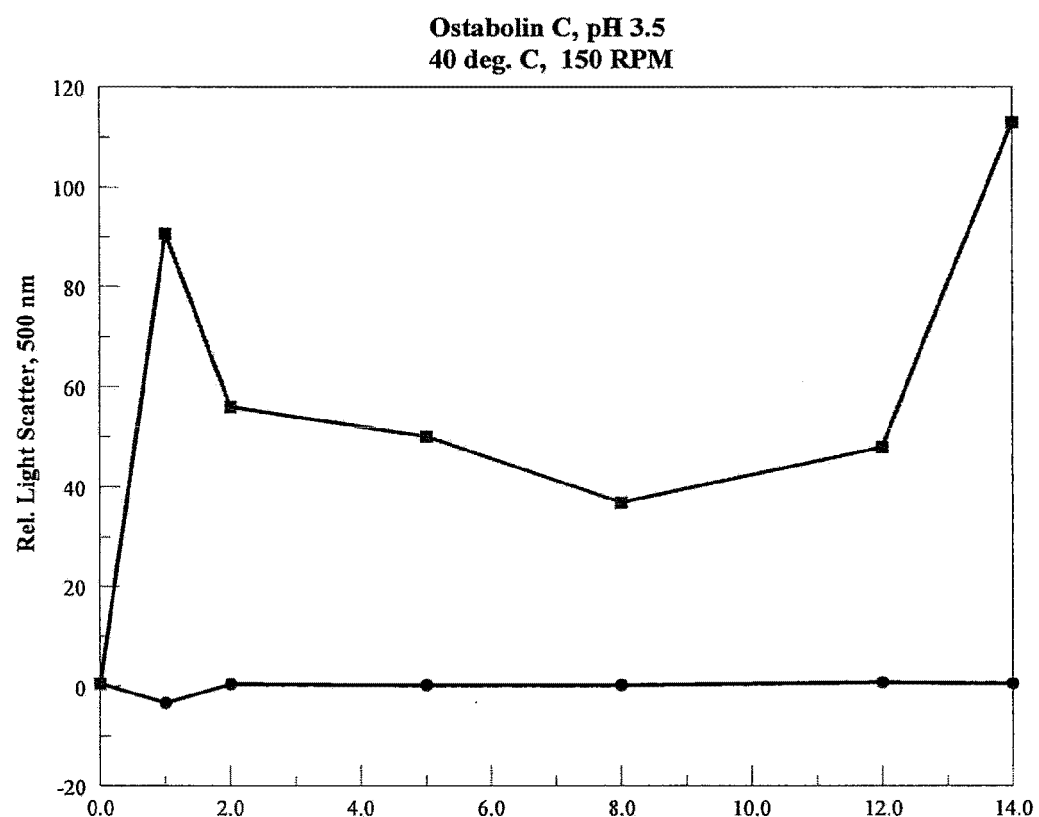
FIG. 8 is a graph showing light scatter readings for the polypeptide Ostabolin C™ (cyclic PTH 1-31) at pH 3.5, admixed with (lower line) and without (upper line) dodecyl maltoside (DDM).
Figure 9:
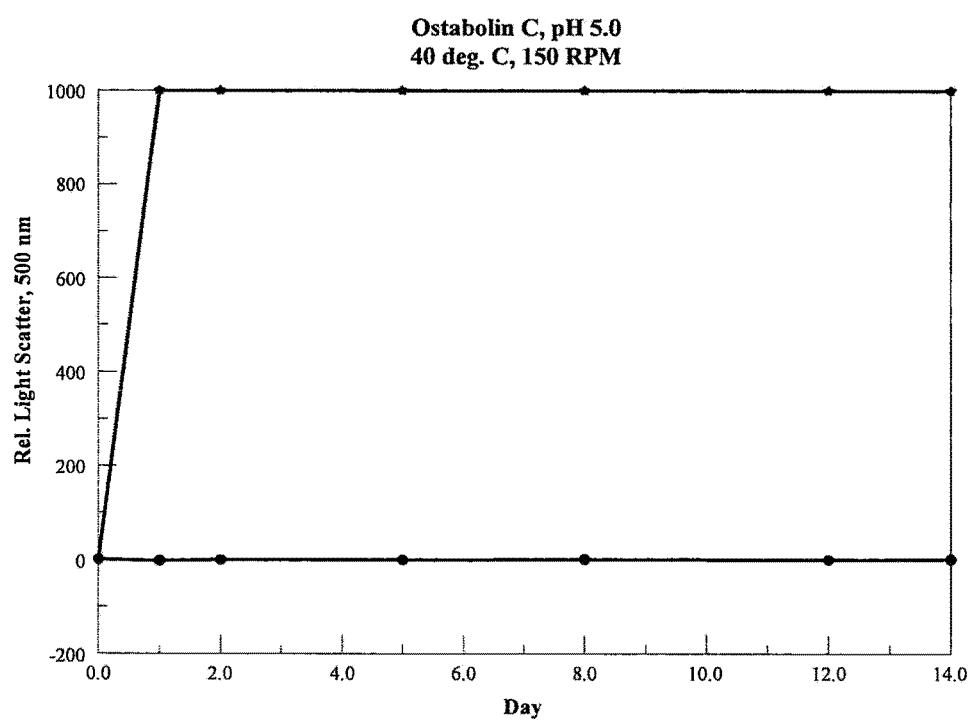
FIG. 9 is a graph showing light scatter readings for the polypeptide Ostabolin C™ (cyclic PTH 1-31) at pH 5.0, admixed with (lower line) and without (upper line) dodecyl maltoside (DDM).
Figure 10:
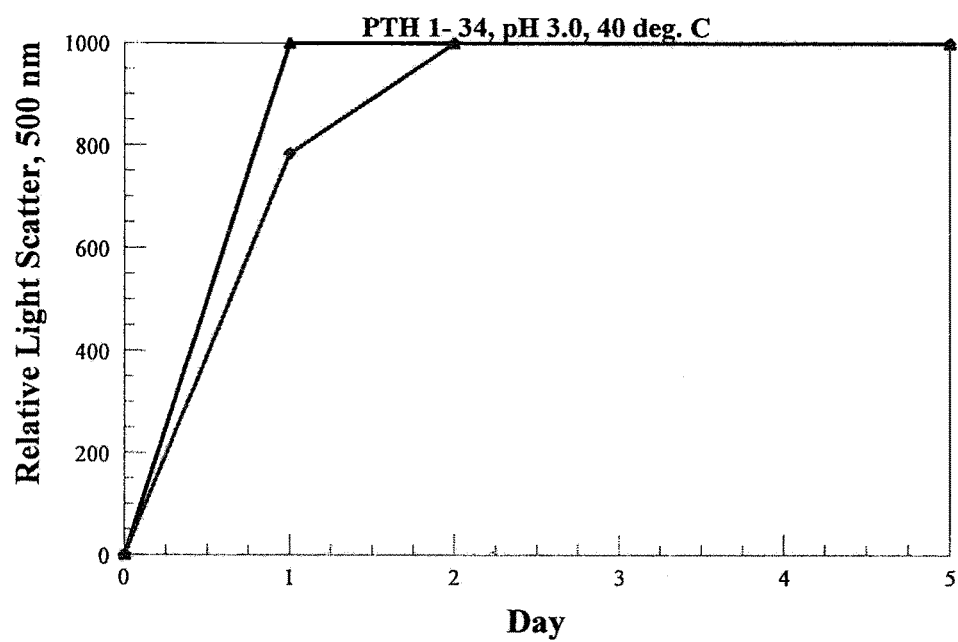
FIG. 10 is a graph showing light scatter readings for the polypeptide PTH 1-34 at pH 3.0, admixed with (lower line) and without (upper line) dodecyl maltoside (DDM).
Figure 11:
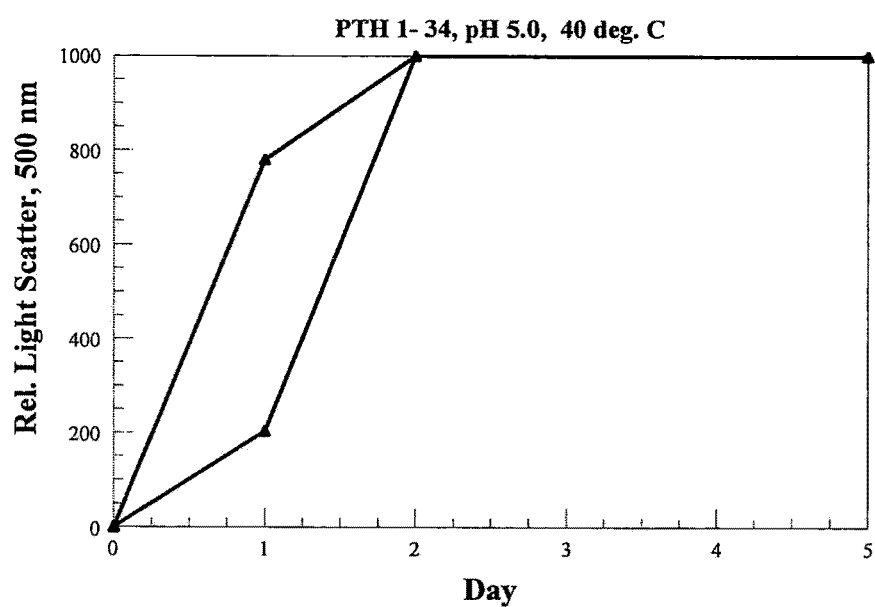
FIG. 11 is a graph showing light scatter readings for the polypeptide PTH 1-34 at pH 5.0, admixed with (lower line) and without (upper line) dodecyl maltoside (DDM).

Until now, the ability of the individual anomers of a particular alkylglycoside used as a surfactants to stabilize a drug composition has not been studied. The present invention is based, in part, on the discovery that the α and β anomers of an alkylglycoside differ in their ability to stabilize compositions including drugs. While both anomers have some capacity to stabilize compositions including drugs, the α anomer of an alkylglycoside is a poor stabilizer (FIG. 7). For example, a composition including insulin admixed with dodecyl α-D-maltoside containing less than 10% dodecyl β-D-maltoside remains stable for approximately 14 days, at which point the composition begins to destabilize. However, a composition including insulin and dodecyl β-D-maltoside with less than 1% contamination of dodecyl α-D-maltoside remains stable for approximately 82 to 88 days. Presence of the α anomer of an alkylglycoside decreases the ability of the β anomer to stabilize a drug. Accordingly, the less α anomer contamination of the β anomer of an alkylglycoside used as a surfactant, the longer the composition remains stable.

Commercially available alkylsaccharides for use in pharmaceutical compositions or formulations typically include a mixture of both α and β anomers. Even when desirable to order a single anomer, typical lot stocks are contaminated by either the α or β anomer. For example, analysis of stock solutions of dodecyl β-D-maltoside from commercially available sources, indicate that stock solutions of dodecyl β-D-maltoside are typically contaminated with about 2% to 10% of dodecyl α-D-maltoside.

Thus, in one aspect of the present invention, the alkylglycoside used is a substantially pure alkylglycoside. As used herein "substantially pure" refers to the β anomer form with less than about 2% of the α anomer form, preferably less than about 1.5% of the α anomer form, and more preferably less than about 1% of the α anomer form. In one aspect, a substantially pure alkylgycoside contains greater than 98% β anomer. In another aspect, a substantially pure alkylgycoside contains greater than 99%β anomer. In another aspect, a substantially pure alkylgycoside contains greater than 99.5% β anomer. In another aspect, a substantially pure alkylgycoside contains greater than 99.9% β anomer.

The compositions of the present invention comprising of at least one drug and at least one surfactant, wherein the surfactant is further comprised of at least one alkylglycoside, can be administered in a format selected from the group consisting of a drop, a spray, an aerosol, a lyophilizate, an injectable, and a sustained release format. The spray and the aerosol can be achieved through use of the appropriate dispenser. The lyophilizate may contain other compounds such as mannitol, gelatin, biocompatible gels or polymers. The sustained release format can be an ocular insert, erodible microparticulates, swelling mucoadhesive particulates, pH sensitive microparticulates, nanoparticles/latex systems, ion-exchange resins and other polymeric gels and implants (Ocusert, Alza Corp., California; Joshi, A., S. Ping and K J. Himmelstein, Patent Application WO 91/19481).

The present invention mitigates and, in some cases, may eliminate the need for organic solvents. Trehalose, lactose, and mannitol have been used to prevent aggregation. Aggregation of an anti-IgE humanized monoclonal antibody was minimized by formulation with trehalose at or above a molar ratio in the range of 300:1 to 500:1 (excipient:protein). However, the powders were excessively cohesive and unsuitable for aerosol administration or exhibited unwanted protein glycation during storage (Andya 1999). Each of the additives discovered have limitations as additives to therapeutics including xenobiotic metabolism, irritation or toxicity, or high cost. The present invention provides excipients that are effective, non-irritating or toxic, do not require xenobiotic metabolism since they are comprised of the natural sugars, fatty acids, or long chain alcohols, and which may also be used to minimize aggregation in aqueous solutions or upon aqueous reconstitution of dried peptide or protein formulations in situ physiologic aqueous reconstitution by aqueous body fluids such as saliva.

In another embodiment, the invention provides methods of administering to a subject in need thereof an effective amount of the therapeutic compositions of the present invention. As used herein, "therapeutically effective amount" is interchangeable with "effective amount" for purposes herein, and is determined by such considerations as are known in the art. The amount must be effective to achieve a desired drug-mediated effect in the treated subjects suffering from the disease thereof. A therapeutically effective amount also includes, but is not limited to, appropriate measures selected by those skilled in the art, for example, improved survival rate, more rapid recovery, or amelioration, improvement or elimination of symptoms.

In one aspect of the present invention, a method of increasing the shelf-life of a drug composition by admixing a drug with a surfactant comprising of at least one alkylglycoside and administering the composition to a vertebrate is described. As used herein, the phrase "shelf life" is broadly described as the length of time a product may be stored without becoming unsuitable for use or consumption. The "shelf life" of the composition described herein, can also indicate the length of time that corresponds to a tolerable loss in quality of the composition. The compositional shelf life as used herein is distinguished from an expiration date; "shelf life" relates to the quality of the composition described herein, whereas "expiration date" relates more to manufacturing and testing requirements of the composition. For example, a composition that has passed its "expiration date" may still be safe and effective, but optimal quality is no longer guaranteed by the manufacturer.

Shelf life is affected by light transmission, gas transmission, heat transmission, humidity transmission, or mechanical stresses. Nearly all chemical reactions will occur at common temperatures. These breakdown processes characteristically happen more quickly at higher temperatures. The usually quoted rule of thumb is that chemical reactions double their rate for every 10 degree Celsius increase in temperature. The reason has to do with activation energy barriers. Compositions described herein allow the peptide or protein to retain at least twice the level of biological activity after storage at 25 degrees Celcius for at least one month. Other methods of increasing shelf life are known in the art and are encompassed in the present application in so much as they increase the shelf life of the described compositions.

Another aspect of the invention provides light scattering as a non-destructive technique for characterizing the state of macromolecules. Light scattering can be routinely used to examine a range of macromolecules including their oligomeric (i.e., aggregated) states. Most importantly, light scattering permits measurement of the solution properties of macromolecules. The intensity of the scattered light can measured as a function of angle or can be measured at fixed angles. For example a filter fluorometer in which the excitation light path is normally set at 90 degrees to the detection light path, and in which the filters are chosen to allow passage of the same light wavelength, can be used as a convenient means to measure light scattering. For the case of macromolecules, light scattering is often called Rayleigh scattering and can yield the molar mass and rms radius of the monomer or aggregate. Aggregates may vary widely in size up to formation of directly visible cloudiness (a light scattering phenomenon) or visible precipitates. Still, other methods including sedimentation equilibrium by ultracentrifugation may be used to observe aggregation directly.

In one embodiment, the present invention relates to a method for chemically modifying a molecule to increase or sustain the biological activity of the composition or molecule, for example, receptor binding or enzymatic activity. The molecule is preferably, although not necessarily, a polypeptide. The method can include binding the molecule in the composition to a polymer such as polyethylene glycol.

The method(s) includes all aspects of the compositions described herein including but not limited to compositions which reduced or eliminate immunogenicity of peptide or protein drugs, are non-irritating, have anti-bacterial activity, increased stability or bioavailability of a drug, decrease the bioavailability variance of that drug, avoid first pass liver clearance and reduce or eliminate any adverse effects. As used herein, the term "immunogenicity" is the ability of a particular substance or composition or agent to provoke an immune response. The immunogenicity of the peptides of the invention can be confirmed by methods known in the art.

In another aspect of the present invention, a method of administering a drug composition comprising of at least one alkylglycoside mixed with at least one drug and delivered to a vertebrate, wherein the alkyl has from 9 to 24 carbon atoms, or further in the range of 10 to 14 carbon atoms, and the surfactant increases the stability and bioavailability of the drug.

The methods of the present invention wherein the surfactant has a high NOAEL which is many times higher than the daily recommended intake amount of that surfactant. For example, the NOAEL is from 10× to 1000× higher than the daily intake amount of the surfactant.

In another aspect of the present invention, a method of reducing or eliminating immunogenicity of a peptide or protein drug composition by admixing the drug with a surfactant comprising of at least one alkylglycoside and/or sucrose ester, wherein the alkyl has from 10 to 14 carbon atoms.

The methods of the present invention are delivered to a vertebrate subject in need of treatment including but not limited to, for example, a human. Moreover, depending on the condition being treated, these therapeutic compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; such as intranasal; buccal; vaginal; rectal; as well as parenteral delivery, including intramuscular, subcutaneous, intravenous, intraperitoneal, or intranasal administration.

It will be understood, however, that the specific dose level and frequency of dosage for any particular subject in need of treatment may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Other formulation components could include buffers and physiological salts, non-toxic protease inhibitors such as aprotinin and soybean trypsin inhibitor, alpha-1-antitrypsin, and protease-inactivating monoclonal antibodies, among others. Buffers could include organics such as acetate, citrate, gluconate, fumarate, malate, polylysine, polyglutamate, chitosan, dextran sulfate, etc. or inorganics such as phosphate, and sulfate. Throughout this application, various publications are referenced. One skilled in the art will understand that the referenced disclosures of these publications are hereby incorporated by reference into this application in order to more fully describe the state of the art to which this invention pertains.

Throughout this application, various publications are referenced. The disclosures of these publications in their entireties are hereby incorporated by reference into this application in order to more fully describe the state of the art to which this invention pertains.

The present invention is more particularly described in the following examples which are intended as illustrative only since numerous modifications and variations therein will be apparent to those skilled in the art. The following examples are intended to illustrate but not limit the invention.

EXAMPLE 1

Insulin Compositions Having Reduced Immunogenicity

To six groups of three Sprague-Dawley rats (Charles River, Charlotte, N.C.) weighing between 300 and 350 grams each is administered either: 1) multiple intranasal (i.n.) doses of insulin in pH 6.0 in 5 mM sodium acetate buffer, 0.9% saline, 0.18% dodecyl maltoside (Buffer A1) or 0.125% sucrose monododecanoate (Buffer A2); 2) an intranasal control comprised of insulin in pH 6.0 in 5 mM sodium acetate buffer, 0.9% saline (i.e., containing no alkyl saccharide (Buffer B); 3) multiple subcutaneous injections (s.c.) of insulin in Buffer A, and; or 4) multiple subcutaneous injections (s.c.) of insulin in Buffer B. The intranasal and subcutaneous doses of insulin (0.5 U insulin per rat) are administered once weekly and an equivalent amount (0.5 U) of insulin is administered in a volume of 20 microliters intranasally or 100 microliters by subcutaneous injection. A 3 mL aliquot of each of the above solutions is lyophilized in a 21×70 mm amber 4 dram screw-top vial by first freezing the vials and contents and placing them in a Labconco Freezon 4.5 lyophilizer in a Labconco 750 mL glass lyophilization vessel for 36 hours.

Each rat is bled weekly for 12 weeks prior to the next administration of insulin. A 500 µl blood sample is drawn by orbital bleed into serum capillary collection tubes. After blood collection, serum is prepared from each blood sample following coagulation by centrifugation of the capillary tubes. All serum samples are stored at −70° C. prior to antibody determination.

Human insulin (recombinant, expressed in *E. coli*, Sigma-Aldrich, St. Louis, Mo.) solutions prepared in pH 6 Na acetate buffer, 5 mM, 0.9% NaCl with (Buffers A) or without (Buffers B) 0.125% dodecyl maltoside (DDM) or sucrose dodecanoate (SDD). Insulin solutions are made on day 1 of the study and stored thereafter at room temperature for the duration of the experiment.

For sample collection, rats are anesthetized with 2% Isoflurane in a Plexiglas anesthesia induction box to facilitate blood collection and insulin administration.

Assay of anti-human insulin antibodies: Assay of anti-human insulin antibodies is conducted using Immunodiagnostic Systems Limited (IDS, Fountain Hills, Ariz.) anti-human insulin ELISA kit with the modification that the alkaline phosphatase labeled goat anti human IgG is replaced with alkaline phosphatase labeled goat anti-rat IgG (Sigma-Aldrich). Human insulin is immobilized onto microwells. The positive control, negative control, and diluted patient serum samples are added to the appropriate microwells. Rat IgG antibodies specific to human insulin in the rat serum sample and controls bind to the insulin molecules on the microwells. After washing off unreacted serum materials, an enzyme (alkaline phosphatase) labeled goat antibody specific to rat IgG is added to the antigen-antibody complex. After thorough washing to remove the unbound enzyme, a substrate, para-nitrophenyl phosphate (PNPP), solution is added and the color development is scored visually. Two quality controls (positive and negative) are provided to monitor and validate assay results. No observed color change in comparison to the negative control is scored as (−). Visible color development is scored on an increasing scale ranging from +/−, +, ++, +++. The intensity of the color is directly proportional to the concentration of anti-insulin antibody.

No antibody is observed at the initiation of the study. After 2-3 weeks, antibody titers are seen to develop in the groups given the non-alkylglycoside formulations. The titers increase over the subsequent weeks. See Tables II and III below. Based on relative ELISA titers, it is seen that formulations containing alkylglycosides result in lower antibody responses.

Lyophilized formulations are reconstituted with 3 mL of water to give the same concentration of drug as that prior to lyophilization. Upon administration of the lyophilized and reconstituted formulations to a second set of six groups of 3 rats per group and collection of blood samples as describe previously, the formulations containing alkylglycosides show essentially no immunogenicity whereas the formulations containing no alkylglycosides elicit a similar antibody response to that seen in the non-lyophilized, non-alkylglycoside containing formulations. Thus lyophilization and reconstitution do not result in increased immunogenicity in the presence of alkylglycosides, but do so in the absence of alkylglycosides.

TABLE II

Immunogenicity upon Intranasal Delivery of Insulin in the Presence of dodecyl maltoside (DDM), an alkylglycoside

| Week | 0.18% DDM Buffer A1 (i.n.) | No alkylglycoside Buffer B (i.n.) | 0.18% DDM Buffer A1 (s.c.) | No alkylglycoside Buffer B (s.c.) |
|---|---|---|---|---|
| | Average Antibody Titers (n = 3 rats) | | | |
| 0 | − | − | − | − |
| 1 | − | − | − | − |
| 2 | − | − | − | + |
| 3 | − | − | − | + |
| 4 | − | + | − | ++ |
| 5 | − | ++ | + | ++ |
| 6 | − | ++ | − | ++ |
| 7 | + | + | − | + |
| 8 | − | ++ | +/− | +++ |
| 9 | − | ++ | − | ++ |
| 10 | +/− | +++ | − | +++ |
| 11 | − | ++ | + | ++ |
| 12 | − | +++ | − | +++ |

TABLE III

Intranasal Delivery of Insulin in the Presence of sucrose mono-dodecanoate (SDD), an alkylglycoside

| Week | 0.125% SDD Buffer A2 (i.n.) | No alkylglycoside Buffer B (i.n.; same control data as above) | 0.125% SDD Buffer A2 (s.c.) | No alkylglycoside Buffer B (s.c.; same control data as above) |
|---|---|---|---|---|
| | Antibody titers | | | |
| 0 | − | − | − | − |
| 1 | − | − | − | − |
| 2 | − | + | − | + |
| 3 | − | + | − | + |
| 4 | − | + | − | ++ |
| 5 | − | ++ | +/− | ++ |
| 6 | − | ++ | − | ++ |
| 7 | +/− | + | − | + |
| 8 | − | ++ | + | +++ |
| 9 | − | ++ | − | ++ |
| 10 | +/− | +++ | − | +++ |
| 11 | − | ++ | + | ++ |
| 12 | − | +++ | − | +++ |

EXAMPLE 2

Insulin Alkyl Saccharide Compositions Have Extended Shelf Life

The effectiveness of insulin formulations may be demonstrated in the Ob-Ob mouse model of diabetes by performing a glucose tolerance test. In a glucose tolerance test a bolus of glucose is administered to the Ob-Ob diabetic mouse by intraperitoneal injection. Because the animal is diabetic, the glucose levels remain elevated for an extended period of time. Upon intranasal administration of insulin (20 microliters containing 0.5 U, administered to a single nare) to the Ob-Ob mouse at the time of the glucose bolus administration, blood glucose levels are seen to return to normal levels much sooner. As the insulin formulation ages, insulin looses activity as a result of self aggregation. In the presence of DDM and SDD, the insulin formulations are seen to retain activity. See the Table below.

TABLE IV

Insulin in the Presence of alkylglycoside formulations has Longer Activity

| | Time (min) | | | | | | | | |
|---|---|---|---|---|---|---|---|---|---|
| | 0' | 15' | 30' | 45' | 60' | 90' | 120' | 180' | 240' |
| | Blood glucose levels, mg/dL | | | | | | | | |
| No alkyl-glyco-side T = 0 days | 190 | 430 | 495 | 370 | 320 | 270 | 218 | 172 | 170 |
| No alkyl-glyco-side T = 28 days | 190* | 435 | 495 | 380 | 343 | 305 | 250 | 200 | 195 |
| 0.125% DDM T = 0 days | 190* | 270 | 355 | 305 | 230 | 195 | 170 | 180 | 180 |
| 0.125% SDD T = 28 days | 190* | 275 | 340 | 310 | 225 | 190 | 170 | 175 | 170 |

TABLE IV-continued

Insulin in the Presence of alkylglycoside formulations has Longer Activity

| | Time (min) | | | | | | | | |
|---|---|---|---|---|---|---|---|---|---|
| | 0' | 15' | 30' | 45' | 60' | 90' | 120' | 180' | 240' |
| 0.18% DDM T = 28 days | 190* | 273 | 345 | 295 | 225 | 200 | 180 | 170 | 173 |

*All subsequent groups' initial glucose levels are normalized to 190 for intragroup comparison.

EXAMPLE 3

TFE Effectively Reduces Fibril Formation and Aggregation

In one embodiment of the invention, there is provided methods to prepare peptide T or analogs thereof, e.g., D-Ala-Peptide T-amide (DAPTA) solutions. In one aspect of the invention, the peptide T or analogs thereof, are of high potency, or bioactivity, and free from fibrils. The fibril formation is, in part, dependent upon salt, temperature, manufacturing, and peptide concentration. However, other physiochemical elements which contribute to fibril formation are contemplated. The following describes a method for reducing or inhibiting fibril formation in peptide T and/or analogs thereof. The methods described herein provide for peptide T and/or analog formulations thereof that are 10-fold greater in potency and bioactivity than peptide T and/or analog formulations in the absence of such conditions or medium. For example, the peptide T or analog formulations thereof, have improved or enhanced or increased blood concentration of the peptide, e.g., increased blood concentrations of DAPTA.

Circular dichroism (CD) studies show that there is threshold concentration near or about or below 0.1 mM, whereby the rate of fibril formation is greatly reduced. The peptide T or analog formulations described herein involve but are not limited to adjusting the DAPTA concentration to be near or below 0.1 mM.

Additionally, it has been determined that deleting the NaCl, commonly used in government and industry trial formulations, greatly inhibits gellation of peptide T formulations. The mixing of the aqueous/alcohol solution with the solid peptide T occurs immediately (i.e. before the first application). The mixing can occur in a bottle or device designed to allow mixing and holding enough solution for a short period of time, e.g., less than 1 day, less than one week, less than two weeks, less than three weeks and the like. Once reconstituted, the peptide T formulation, or drug, should be at room, or ambient temperature.

The fibril formation process is thought to initiate from a slowly forming nucleation seed, which is poorly defined. However, once initiated, extension and then stacking can proceed much more rapidly. Hence, one aspect of the methods described herein is to remove any nucleation seeds, thus preventing fibril formation. The nucleation seeds can be various contaminants or nascent aggregates from the manufacturing process, for example, lyophilizing the peptide. Different manufacturing processes or even unpredictable and uncontrolled batch to batch variability in the same manufacturing process may yield more or less nucleation seeds as illustrated in the examples which follow. Various methods to remove the contaminants or aggregates include, but are not limited to, micro-filtration, ultrafiltration, affinity chromatography, selective absorption chromatography, ion exchange chromatography, lyophilization, dialysis, and precipitation or salting-out.

Still, the methods described herein encompass those solvents which disrupt peptide fibril or aggregate structure, for example, by inducing formation of alpha-helixes, and thereby removing or preventing fibril formation. Trifluoroethanol (TFE) and 1,1,1,3,3,3-hexafluoro-2-propanol (HFIP) have been shown to have this property for amyloids and other peptides. The invention also encompasses various variants, mutations (e.g., deletions) which will stabilize a peptide and prevent fibril formation. For example, the so-called amyloid-β (e.g., 1-42 residues) peptide associated with Alzheimer's disease is highly fibrillogenic, while peptides lacking residues 14-23 are not (Tjernberg et al., 1999, J. Biol. Chem. 274:12619-12625). Similarly, peptide T and/or analogs thereof, including DAPTA, may therefore contain deletions and/or mutations as compared to the wild-type sequence which stabilizes fibrils and or inhibits, reduces or prevents fibril formation.

Moreover, the methods of peptide T or analog formulation described herein may undergo various filtration steps and additional admixing steps with solvents prior to a final finishing step or a final lyophilization from solvents. The method described herein can also encompass additional steps such as modifying pH, addition of salts, etc which block or remove nucleation seeds. The method described herein can utilize an antibody or a peptide or agent which stabilizes the unstable or discordant helix, or specific region of a discordant helix by binding to that region and allow for stability. Identified substances are then tested for their ability to inhibit fibril formation, e.g., stabilize α-helical conformation. Another approach to identifying compounds that inhibit fibril formation and/or stabilize the α-helical conformation is to screen chemical libraries for molecules that inhibit fibril formation and stabilize an α-helical conformation using methods such as those described herein. Thus, methods described herein encompass an assay for detection of fibril formation of a drug, or peptide T or analog thereof, e.g., DAPTA, in the presence and absence of a test compound, e.g., a compound identified from a chemical library above, to prescreen test compounds for those that are to be used in subsequent assays of α-helix stabilization. Similarly, the ability of a candidate compound to inhibit fibril formation can be used to confirm the predicted efficacy of a candidate compound in preventing fibril formation.

Concentrations of 5 mgs per mL, 0.5 mgs per mL, and 0.05 mgs per mL and below with or without the addition of GRAS (i.e., so-called in FDA regulations as Generally Recognized As Safe) reagents such as but not limited to EDTA, buffers, preservatives, chelators, and the like, as well as alkyl glycosides and/or alkyl saccharides described may be used to further suppress and prevent fibril formation. Simple sugars, by virtue of their alcoholic groups (—OH) may disrupt bonding leading to stacking as the DAPTA peptide is rich in threonines which contain (—OH) groups. Modifications in the peptide primary sequence, or side groups to reduce intermolecular bonding, would be useful, and are contemplated. These improvements will enhance potency, requiring less drug to be administered, and extend the useful storage period of the drug.

Fibril formation can be monitored by examining the spectropolarimetric shift, elecronmicroscopy studies, and/or other methods, e.g., dye-binding techniques, as described herein. Additionally, biological testing, for specific activity, as an antiviral (Ruff, M R, et al., 2001), chemo-attractant (Redwine, 1999), agonist or antagonist of MAPkinases (Ruff, pert, Meucci, unpublished data), or transcription factors, for example, can also be used.

Biophysical studies revealed that DAPTA has a tendency to form fibrillar aggregates in aqueous solutions, similar or identical to those used in the formulation of DAPTA in prior clinical trials. These fibrillar aggregates are biologically inactive, and would be expected to have distinctly different pharmacokinetic and pharmacodynamic properties from the monomer. The detailed study of the DAPTA aggregates and DAPTA fibril formation in aqueous solutions is described herein.

Peptide Storage. Peptides were stored at −20 deg. C. as dry powders, from the stated dates of synthesis.

Preparation of DAPTA solutions. DAPTA was dissolved in water, and solutions maintained at various temperatures and times. To prepare fibrils, DAPTA was prepared at 10 mgs/mL in water and stored overnight at 4° C.

Determining fibril formation. Fibril formation of peptide T or analog thereof can be determined using electron microscopy. A 2 µl aliquot of the DAPTA solution in water was applied to a formvar/carbon coated nickel EM grid. The grids were rinsed x3 with 10 µl distilled water and stained with 10 µl of 2% uranyl acetate. The samples were examined on an FEI TEM Tecnai microscope with a LaB6 filament (120 kv) and imaged with a Megaview II CCD camera.

Fibril formation of peptide T or analog thereof can also be determined using dye binding. Congo red was dissolved in PBS (5 mM potassium phosphate, 150 mM NaCl, pH 7.4) to a concentration of 7 ug/mL. The solution was chilled to 4° C., and DAPTA added as a 10 mg/mL stock solution in water, to yield final peptide concentration in the dye solution of 0.48 mg/mL. Peptide solution immediately after dissolution of powder was compared with an aged stock solution containing aggregated peptides. Spectra were collected between 400-700 nm, at 4° C.

Fibril formation of peptide T or analog thereof can also be determined using Circular Dichroism (CD) spectroscopy. Ten mg/mL solutions in water of either freshly prepared peptide or containing fibrillar aggregates was added to distilled water at 4° C. to a concentration of 50 ug/mL. CD spectra were collected on a Jasco model J-810 spectrometer using a 0.1 cm path length quartz cuvette, between 190-250 nm, with a 1 min interval, and a response time of 2 sec.

Still another method of determining fibril formation of peptide T or analog thereof is performed using Fourier Transform Infrared (FTIR) Spectroscopy. DAPTA was dissolved in deuterated water, to a concentration of 10 mg/ml and incubated under temp and time conditions that promote fibril formation. 25 ul samples were then placed in a pre-cooled transmission cell with NaCl windows separated by a 6 um spacer. FTIR spectra were collected on a BioRad FTS-175C Fourier transform spectrometer in transmission mode using a DTGS detector. 2506 interferograms were recorded with a 2 cm-1 resolution. Water vapor was subtracted and the spectra baselines corrected.

The results were as follows. Peptide T or an analog thereof, e.g., DAPTA, aggregates in solution, in some cases into well-ordered bundles. Fibril formation has been followed by the various techniques described herein (e.g., EM, FTIR, CD and dye binding). Preliminary X-ray diffraction studies suggest that ordered fibrillar aggregates are composed of peptides, packed in narrow parallel arrays of β sheets, and stacked perpendicular to the long axis of the fibril (FIG. 1).

In solution, DAPTA can be shown to form ordered aggregates by EM, FTIR, and CD and dye binding. Aggregation is promoted by concentration, increased ionic strength, and reduced temperature. Although the kinetics of aggregation appear to vary, from preparation to preparation, aggregation appears to be a property associated with all batches of DAPTA examined as measured by EM.

Fibrillization can be observed in solutions prepared in 0.9% saline (10 mg/mL) when stored at 4° C. in less than 1 hour. At room or ambient temperature, fibril formation can be observed within 48 hours, although there is variation from preparation to preparation. In distilled water, DAPTA solutions at 10 mg/ml readily form aggregates at 4 deg. C., within 2 hrs, and at room temperature, within 1-7 days.

Aggregation is discovered to be associated with a loss of biological activity in vitro. Typically, the recommended protocol is to have DAPTA stored at 0.1 mM solutions in water at 4° C. However, DAPTA under these conditions was found to form fibrils as observed and confirmed by EM and disclosed herein. DAPTA stored under these conditions was observed to have reduced activity event though the chemical integrity of the peptide appears unchanged as measured by HPLC; and by about 6 weeks, the DAPTA formulation exhibits substantial loss of activity as measured by HIV uptake inhibition in vitro as disclosed in the Examples which follow. Thus, currently recommended protocols, which maintain DAPTA at 0.1 mM concentration solutions or lower, at 4° C., create peptide aggregates and form inactive preparations.

In one embodiment, aqueous solutions of aggregated peptides can be partially dissociated by warming the peptide aggregates, for example, DAPTA solutions at 5 mg/mL in 0.45% NaCl reversibly dissociate when solutions are warmed to 37° C., for about 17-24 hours, e.g., 17-18 hours with shaking. The experiment was done in parallel except shaking was performed at room or ambient temperature. Treatment with TFE over time and heat drives substantially all DAPTA into an alpha-helical conformation and out of β-sheet forms, which DAPTA favors, and hence dissociates DAPTA into monomers. Thus, substantially all aggregation seeds having at least 2, or 2 or more molecules of DAPTA to form β-sheets. Following reduction or inhibition of β-sheet formation, the DAPTA solution can then be lyophilized without aggregation. The lyophilized peptide can then be reconstituted in water and the like, and is capable of being stored in water for an extended period of time.

Aggregation is reduced in the presence of trifluoroethanol (TFE). TFE was selected because of its property of reducing certain types of protein-protein interactions. DAPTA was dissolved in either distilled water, or solutions containing between 60% and 100% TFE. Aggregation was evaluated by assaying inhibition of HIV infectivity, in vitro. DAPTA stored in solution with TFE at concentrations between 60% and 100% retained more activity as compared to DAPTA stored in the absence of TFE or in water under equivalent conditions. Also, TFE is capable of disassociating preformed aggregates of DAPTA. Aggregates of DAPTA, formed in distilled water were disrupted by addition of TFE to 80%, as measured by EM.

EXAMPLE 4

DAPTA Compositions with TFE and/or Alkyl Glycosides have Increased Bioactivity and Extended Shelf Life In "in vitro" studies, DAPTA it has been reported to prevent HIV from infecting CD4 cells by blocking receptor sites on the CD4 molecule (Bridge et al. 1989; Pert and Ruff 1986; Pert et al. 1988; Ruff et al. 1987; Ruff et al. 1991). DAPTA is an octa-peptide which mimics and competes with both a section of VIP and a section of gp120, the HIV surface molecule which binds to the CD4 receptor. Brenneman et al. (1998) reported that DAPTA and VIP can prevent gp120-induced neuronal cell death "in vitro". Simpson et al. (1996) reported that in a phase II double-blind efficacy trial of DAPTA, there were no statistically significant differences between DAPTA (6 mg/day for 12 weeks) and placebo in the treatment of painful peripheral neuropathy.

The drug also seemed to have no effects on neuropsychological functions. The study enrolled 81 participants with AIDS. Heseltine et al., (1998) treated 215 people with mild to severe cognitive impairment with either DAPTA (2 mg three times daily intranasally) or placebo for six months, followed by open-label DAPTA for an additional six months. Analysis of all people who completed at least four months of treatment showed there was no difference in neuropsychological performance between the two arms. After the analyses were adjusted to take account of an imbalance in baseline CD4 count between the groups, people who received DAPTA showed greater improvement (p=0.07). In particular, DAPTA was beneficial for people with CD4 counts greater than 200 or with more evident cognitive impairment at baseline. Those with a baseline deficit score above 0.5 showed overall cognitive improvements while the placebo group experienced an overall deterioration in cognitive performance. Kosten conducted a placebo-controlled, double-blind, cross-over study of 15 mg or 1.5 mg of DAPTA daily in nine injecting drug users with early AIDS dementia. Neuro-psychological performance improved in 4/5 patients who received high dose DAPTA compared to only 1/4 in the low dose group (Kosten et al., 1997). Participants were also receiving methadone and AZT monotherapy. Bridge et al. (1989) reported a phase I safety and dosing study of DAPTA in 14 people with AIDS. Drug was dosed from 0.1 to 3.2 mg/kg/day intravenously for twelve weeks. The first six patients to complete treatment continued on intranasal drug (25 mg/day for eight weeks). Cognitive and neuromotor function improved in patients with moderate neuro-psychological impairment compared with controls. MacFadden and Doob (1991) reported that of nine individuals with HIV-related peripheral neuropathy treated with DAPTA (subcutaneously at an initial dose of 10 mg daily, with two patients tapered to 2.5 mg in order to determine the minimal effective dose), all experienced either complete or subjectively significant resolution of lower limb pain, with effects being noticed as early as two days after initiation of treatment. The pain-free interval persisted for the duration of the treatment (for 3 to 70 weeks) but pain recurred gradually within one week of stopping the drug, resolving upon reinstitution of treatment. In 2 participants, decreasing the dose to 2.5 mg/day resulted in recurrence of pain, which resolved when the dose was increased to 5 mg. No adverse drug effects were noted.

Cultured monocytes were infected with the SF-163 strain of HIV. The level of P24 antigen was measured in the cell supernatant and is an indication of the presence of infectious virus. In the control designated as virus only control, the concentration of P24 antigen is approximately 154.5 picograms per mL. DAPTA has been seen to aggregate relatively quickly resulting in a significant to nearly complete loss of activity. Thus samples 13, 14 and 15, which were aged for seven days before use, exhibit concentrations of P24 antigen similar to that seen for the virus-only control and thus have essentially no activity. When solutions of DAPTA are prepared in the presence of 80% trifluoroethanol, the solutions remain active for an extended period of time as seen by the reduced levels of P24 antigen. Unfortunately, trifluoroethanol is not a desirable solvent for use in a therapeutic formulation. When dodecyl maltoside or sucrose mono-dodecanoate is added to solutions of DAPTA, the activity is seen to remain for an extended period of time, once again as seen by the reduced levels of P24 antigen. Concentrations of dodecyl maltoside or sucrose mono-dodecanoate used in this experiment were approximately 0.125% to 0.2% per mL. The alkyl saccharides significantly stabilize DAPTA by preventing aggregation and thus increase the shelf life of this very promising anti-HIV therapeutic. See the Table below.

In another embodiment of the invention, DAPTA formulations were admixed in 80% TFE and shaken at 37° C. for about 17-18 hours. The formulations were lyophilized using speedvac, and stored as a lyophilized powder until dissolved in $H_2O$ with or without alkylglycosides. These experiments demonstrate that in the presence of the surfactants described herein, e.g., alkyl glycosides such as dodecyl maltoside (DDM) or sucrose mono-dodecanoate (SDD), there is a significant improvement with regards to reduction of peptide aggregation as compared to parallel studies in the absence of the surfactants.

In one aspect of the invention, TFE can be introduced to DAPTA as a near last step, and the solvent evaporated.

Thus, the invention described herein demonstrates that synthetic preparations of peptide T, e.g., DAPTA, independent of source and date of synthesis, form aggregates as confirmed by spectroscopic methods, e.g., X-ray diffraction, and direct visualization by EM. These peptide aggregates are promoted by increasing peptide concentration, decreasing temperature, increased ionic strength and is time dependent (hours). The in vitro studies show that peptide aggregation reduces the biological activity of the peptide, polypeptide or variant thereof, e.g., DAPTA. Further that use of co-solvents such as TFE or HFIP reduces the formation of aggregates and disrupts preformed aggregates. Lastly, the ordered structure of the peptide aggregates suggests that specific interactions are responsible. Therefore, although TFE is not generally included in pharmaceutical preparations and or therapeutic compositions, its properties lend themselves to the invention described herein. Still, other excipients or agents or co-agents can be included in the peptide therapeutic formulation to inhibit fibril formation or prevent or reduce the aggregation formation.

TABLE V

DAPTA in the Presence of Alkylglycosides Extends Stability and Drug Shelf-Life

| Samples ID | Concentration of DAPTA | p24Ag pg/mL | | Mean | Std Dev |
|---|---|---|---|---|---|
| | No TFE - aged 7 days before use | | | | |
| 1 | 2.5 mg/mL in DDM | 131.104 | 93.545 | 112.325 | 18.78 |
| 2 | 0.5 mg/mL in DDM | 43.208 | 36.435 | 39.822 | 3.39 |
| 3 | 0.05 mg/mL in DDM | 69.993 | 61.372 | 65.683 | 4.3 |
| | No TFE - aged 7 days before use | | | | |
| 4 | 2.5 mg/mL in SDD | 41.361 | 34.588 | 37.975 | 3.4 |
| 5 | 0.5 mg/mL in SDD | 56.601 | 54.599 | 55.6 | 1.00 |
| 6 | 0.05 mg/mL in SDD | 18.887 | 22.735 | 20.811 | 1.9 |
| | From 80% TFE - aged 7 days before use | | | | |
| 7 | 2.5 mg/mL in $H_2O$ | 70.301 | 67.838 | 69.07 | 1.2 |
| 8 | 0.5 mg/mL in $H_2O$ | 70.608 | 75.073 | 72.84 | 2.2 |
| 9 | 0.05 mg/mL in $H_2O$ | 63.22 | 61.219 | 62.2 | 1 |
| | Samples in $H_2O$ - made fresh at time of use | | | | |
| 10 | 2.5 mg/mL made fresh | 12.729 | 8.727 | 10.728 | 2 |
| 11 | 0.5 mg/mL made fresh | 154.656 | 148.807 | 151.73 | 2.9 |
| 12 | 0.05 mg/mL made fresh | 100.625 | 329.063 | Outlier | |
| | Samples in $H_2O$ - aged 7 days before use | | | | |

TABLE V-continued

DAPTA in the Presence of Alkylglycosides Extends Stability and Drug Shelf-Life

| Samples ID | Concentration of DAPTA | p24Ag pg/mL | | Mean | Std Dev |
|---|---|---|---|---|---|
| 13 | 2.5 mg/mL in H₂O | 160.66 | 100.01 | 130.335 | 30.3 |
| 14 | 0.5 mg/mL in H₂O | 96.931 | 65.837 | 81.384 | 15.5 |
| 15 | 0.05 mg/mL in H₂O | 168.51 | 177.284 | 172.897 | 4.4 |
| | Virus only 1:10 | 154.502 | 134.029 | 144.27 | 10.2 |
| | Non treated cells only | −30.218 | −32.681 | 0 | |

EXAMPLE 5

Quantitative Measurement of Protein Stabilization by Alkylsaccharides Using Light Scattering Measurements This study was performed to determine and document the effects of alkylsaccharide surfactants described herein on the aggregation of various proteins in solution at 37° C. at varying pHs. Recombinant human insulin (Humulin-R, manufactured by Eli Lilly) and human growth hormone or hGH (Humatrope, manufactured by Eli Lilly) solutions containing alkylsaccharides were prepared, along with identical control protein solutions without alkylsaccharides. Solutions were incubated at 37° C. on a rotary platform shaker (LabLine thermoregulated shaker) at 150 rpm for up to three weeks. Protein aggregation was determined by measurements of light scatter using a Shimadzu RF-500 recording spectrofluorophotometer with both the excitation and emission wavelengths set at 500 nm. Measurements were taken on Day 0 and at various time intervals during the three week period.

Figure 2:
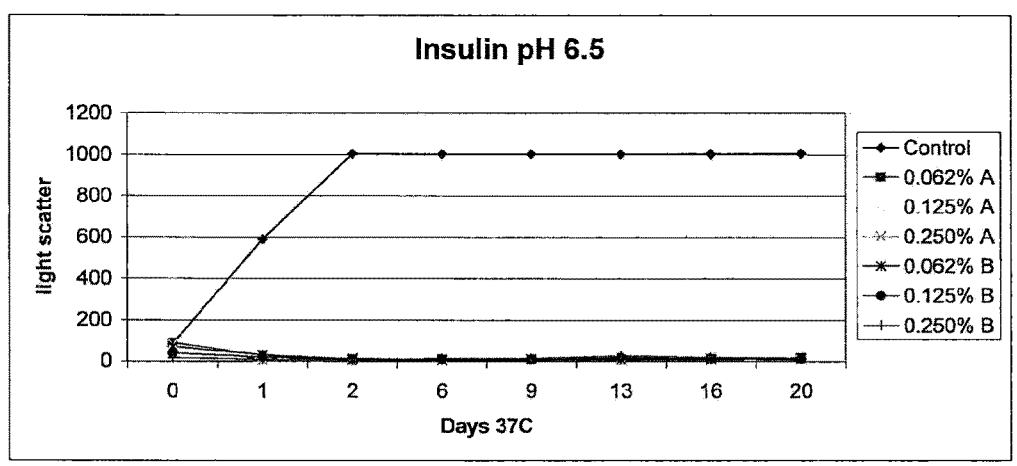
FIG. 2 is a graph showing light scatter readings for the polypeptide insulin at pH 6.5, admixed with "A", mono-dodecanoate (SDD) or "B" dodecyl maltoside (DDM).
Figure 3:
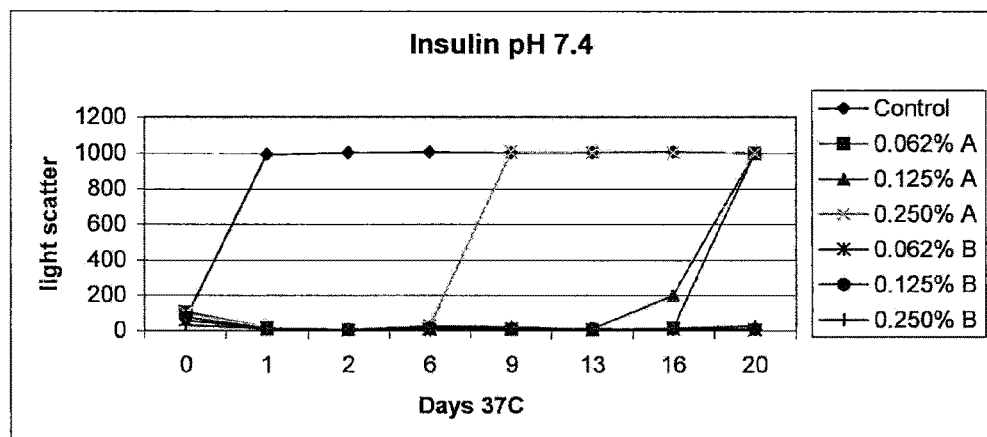
FIG. 3 is a graph showing light scatter readings for the polypeptide insulin at pH 7.4, admixed with "A", mono-dodecanoate (SDD) or "B" dodecyl maltoside (DDM).

Insulin preparations. 25 ml solutions of Humulin-R (insulin) at 0.5 mg/ml and lysozyme at 1.0 mg/ml were prepared in citrate buffer at pH 5.5, 6.5 and 7.4, without and with dodecyl maltoside and sucrose dodecanoate at 0.250%, 0.125% and 0.062% final surfactant concentrations, by dilution of Humulin-R U-100 (Lilly HI-210, 100 units/ml) recombinant human insulin stock solution at 4.0 mg/ml protein. The final buffer composition was: 5 mM Citric Acid+0.1% EDTA, titrated with NaOH to pH 5.5, 6.5 and 7.4. Each solution was stored in a 50 ml glass vial and capped with parafilm. Day 0 light scatter measurements were performed on the insulin samples at pH 6.5 and 7.4, and then the samples were re-sealed with parafilm and incubated at 37° C. with 150 rpm shaking (FIGS. 2 and 3).

Figure 4:
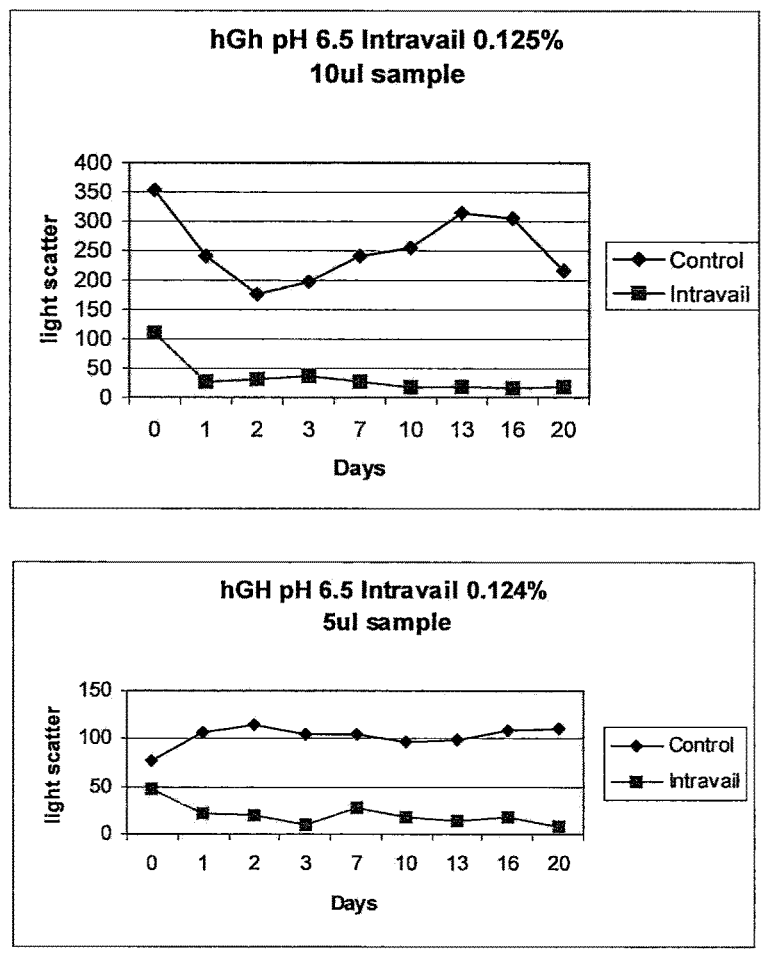
FIG. 4 is a graph showing light scatter readings for the polypeptide human growth hormone (hGH) at pH 6.5, admixed with either 0.124% or 0.125% dodecyl maltoside (DDM).

Human Growth Hormone (hGH) Preparations. Humatrope human growth hormone (hGH) 5 mg lyophilized. The vial of Humatrope was dissolved in 9.0 ml of buffer, then split into two 10 ml glass vials and stored overnight at 4° C. Solubility was good. Buffer was added to the control vial to a final volume of 5 ml. Buffer and dodecyl maltoside from a stock solution were added to the second vial to a final concentration of 0.125% and a final volume of 5 ml. The final buffer composition in each vial was: 5 mM Citric Acid+0.1% EDTA, titrated with NaOH to pH 6.5. The corresponding control solution contained no dodecyl maltoside. Day 0 light scatter measurements were performed on the two hGH samples, and then the samples were re-sealed with parafilm and incubated at 37° C. with 150 rpm shaking (FIG. 4).

Light Scatter Measurements. Light scatter was measured for each protein sample at selected time points during the three week study with a spectrofluorophotometer (Shimadzu model RF-1501). Both excitation and emission wavelengths were set to 500 nm, and samples were read in disposable cuvettes with a 1 cm path length. For each reading, the instrument was zeroed with 1 ml of the appropriate buffer, then an aliquot of protein sample was added, mixed by inverting multiple times, and the cuvette was checked for air bubbles before three stable readings were recorded. The spectrofluorophotometer was set for high sensitivity and the maximum possible reading was 1000 units. Insulin samples at Day 0 were measured with 50 ul aliquots, then with 10 μl aliquots for readings at subsequent time points. Light scatter measurements for the two hGH samples used 5 μl and 10 μl aliquots at Day 0 and at each time point. After light scatter readings were taken, each protein sample was re-sealed with parafilm and returned to 37° C. with 150 rpm shaking. The results are shown in the Table below and FIGS. 2, 3 and 4. Results for insulin at pH 5.5 were essentially the same as pH 6.5 over the 20 day period. In each case, "A" designates dodecyl maltoside; "B" designates sucrose dodecanoate.

TABLE VI

Insulin Light Scatter Measurements (Average of 3 readings)

| | Day 0 | Day 1 | Day 2 | Day 6 | Day 9 | Day 13 | Day 16 | Day 20 |
|---|---|---|---|---|---|---|---|---|
| Insulin pH 6.5 | | | | | | | | |
| Control | 84.8 | 589.1 | 1003 | 1002 | 1002 | 1002 | 1003 | 1005 |
| 0.062% A | 89.2 | 28.6 | 3.6 | 9.7 | 9.3 | 7.0 | 11.7 | 18.2 |
| 0.125% A | 147.3 | 9.0 | 10.5 | 12.5 | 8.7 | 9.9 | 5.3 | 3.7 |
| 0.250% A | 84.1 | 3.7 | 16.0 | 4.1 | 7.5 | 15.0 | 7.0 | 6.5 |
| 0.062% B | 71.3 | 30.3 | 11.2 | 5.3 | 9.2 | 7.6 | 11.4 | 14.8 |
| 0.125% B | 39.1 | 18.5 | 10.7 | 7.8 | 5.8 | 18.1 | 13.2 | 9.3 |
| 0.250% B | 15.8 | 8.7 | 4.5 | 15.0 | 14.9 | 26.2 | 19.8 | 16.3 |
| Insulin pH 7.4 | | | | | | | | |
| Control | 69.6 | 993.9 | 1003 | 1004 | 1003 | 1003 | 1004 | 1000 |
| 0.062% A | 106.1 | 18.7 | 5.5 | 10.3 | 10.0 | 6.8 | 17.0 | — |
| 0.125% A | 104.0 | 10.2 | 10.7 | 11.6 | 8.0 | 12.0 | — | — |
| 0.250% A | 100.2 | 20.0 | 6.5 | 28.6 | — | — | — | — |
| 0.062% B | 57.9 | 16.5 | 2.8 | 7.1 | 11.6 | 7.3 | 8.4 | 4.5 |
| 0.125% B | 77.7 | 11.5 | 7.0 | 14.7 | 11.2 | 11.6 | 7.6 | 10.8 |
| 0.250% B | 32.4 | 11.8 | 7.8 | 26.9 | 22.3 | 10.7 | 14.5 | 29.3 |

A = dodecyl maltoside;
B = sucrose dodecanoate

TABLE VII hGH Light Scatter Measurements
(Average of 3 readings at 5 μL and 10 μL sample sizes)

| hGH pH 6.5 | Day 0 | Day 1 | Day 2 | Day 3 | Day 7 | Day 10 | Day 13 | Day 16 | Day 20 |
|---|---|---|---|---|---|---|---|---|---|
| Control 5 μl | 76.1 | 105.8 | 114.3 | 105.2 | 103.6 | 97.2 | 99.1 | 108.7 | 110.7 |
| 0.125% A 5 μl | 48.0 | 21.4 | 18.5 | 10.2 | 27.5 | 18.2 | 13.9 | 17.7 | 7.3 |
| Control 10 μl | 353.2 | 241.4 | 175.6 | 197.1 | 241.5 | 254.6 | 314.1 | 304.7 | 216.4 |
| 0.125% A 10 μl | 109.7 | 26.4 | 30.9 | 31.0 | 26.9 | 17.0 | 18.1 | 16.0 | 17.5 |

A = dodecyl maltoside

EXAMPLE 6

Tendency of Various Stored Powdered Samples of D-Ala Peptide T Amide (DAPTA) to Form Fibrils Peptides were stored at −20° C. as dry powders, from the stated dates of synthesis, then dissolved in water at a concentration of 10 mgs/ml which has been used in many clinical trials, and solutions maintained at various temperatures and times. Samples were examined by Electron Microscopy using a 2 μl aliquot of the Dapta solution in 0.9% saline applied to a formvar/carbon coated nickel EM grid. The grids were rinsed x3 with 10 μl distilled water and stained with 10 μl of 2% uranyl acetate. The samples were examined on a FEI TEM Tecnai microscope with a LaB6 filament (120 kv) and imaged with a Megaview II CCD camera. By this method, fibrils were most easily and reliably visualized. Of 100 fields examined, +++++ means that fibrils were most readily detected while + means fibrils were rarely detected.
Results:
Phoenix Pharmaceuticals
   April 2003
   Code: 057-03
   Lot #: 20569+++++
Peptech (Europe)-Denmark
   February 1995
   a) lot #171101, product #3022+
   b) Lot #17543++
Calbiotech
   March 1995
   a) Lot #101601++
   b) Lot #101801+
Peptide Technologies Corp.
   3-20+++
Penninsula Labs
   a) GMP #539, Lot #036299+++
   b) Code #9301, Lot #036299+++
   c) Mar. 9, 1995, Lot #022376++++
   d) Code #7444, Lot #801688+++

EXAMPLE 7

DAPTA Time Dependent Loss of Anti-Viral Activity Upon Storage in Solution

Aqueous solutions of DAPTA comparable to clinical formulations (0.1 mM in water) were prepared and their biological potency tested after storage at ambient temperatures for various times. DAPTA was synthesized (Peninsula, Belmont, Calif., 95% pure). Peptide was dissolved at 5 mg/ml in water, stored at ambient temperature, ca 23-27° C., and samples tested for biological activity in an HIV infection assay.

Inhibition of HIV infection is studied by utilizing an infection assay in which GHOST CD4 CCR5 cells are infected with HIV BaL, an R5 tropic isolate (Ruff, M R et al., 2001). Infection is detected via viral induction of the hGFP gene (green fluorescent protein) 48 hrs post-infection. Trays are measured in a plate reader to determine fluorescence intensity. All infections are performed by adding fresh culture medium containing approximately 1,000 infectious units of HIV-1 per well (96-well plates).

Figure 5:
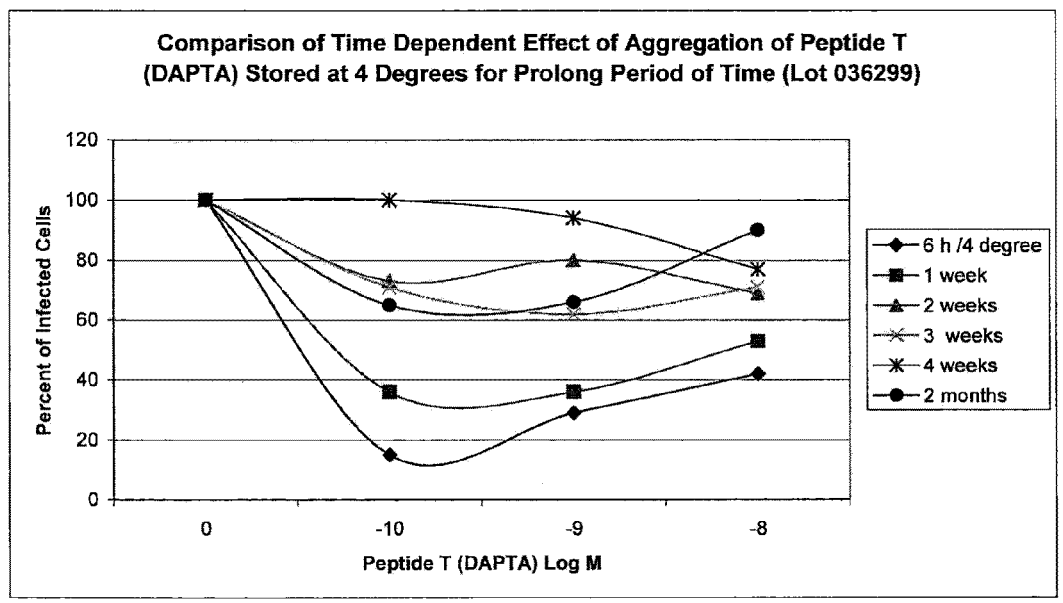
FIG. 5 is a graph showing the time dependent effect of untreated DAPTA aggregation stored for different periods of time at 4 degrees Celcius (6 h ♦) or 25 degrees Celcius (1 ■, 2 ▲, 3 x and 4 * weeks and 2 ● months).

Samples were then aged by storage at ambient temperature (ca 25° C.) for 14 days prior to antiviral testing. The results are shown FIG. 5. In FIG. 5, only the short term 6 hour sample is stored at 4° C., while the other samples are stored at 37° C. FIG. 5 shows that the longer the compositions are stored, the less active it becomes, i.e., the less protective effect on infection Peptide T has.

EXAMPLE 8

Effects of TFE Concentration and Time and Temperature of Treatment on DAPTA Aggregation Effect of TFE Concentration on DAPTA Aggregation.

DAPTA was synthesized by Peninsula Labs, CA (95% pure). The peptide was dissolved in the indicated concentration of TFE in water and then shaken or agitated for 24 hrs at 37° C. See the Table below. The peptide was subsequently dried down, and the TFE/water mixture removed under vacuum. Dried DAPTA was reconstituted or resuspended in an aqueous solution, e.g., water, and stored for about 3 days until the activity of the peptide was assayed for antiviral activity. The studies were done in triplicate using 0.1 nM DAPTA and the results are presented with the mean in Table VIII below. Although TFE is removed, residual traces of TFE within acceptable range for human consumption may remain.

Inhibition of HIV infection was studied by utilizing an infection assay using GHOST CD4 as previously described by Ruff, M R et al., 2001. CCR5 cells are infected with HIV BaL, an R5 tropic isolate. Infection is detected via viral induction of the hGFP gene (green fluorescent protein) about 48 hours post-infection. Trays were measured in a plate reader to determine fluorescence intensity. All infections were performed by adding fresh culture medium containing approximately 1,000 infectious units of HIV-1 per well (96-well plates).

TABLE VIII

Effect of TFE Concentration on DAPTA Aggregation

| TFE Concentration (%) | Percent Reduction in HIV Infection |
|---|---|
| 0 | 0 ± 2 |
| 20 | 0 ± 3 |
| 40 | 0 ± 2 |
| 60 | 20 ± 4 |
| 80 | 100 ± 5 |
| 100 | 98 ± 3 |

Effect of Time Shaking in TFE on DAPTA Aggregation.

DAPTA, as above, was dissolved in about 80% TFE/water solution for and shaken for various periods of time at 37 degrees Celcius. See Table IX below. Again, the peptide was then evaporated or dried down, and resuspended in an aqueous solution, e.g., water for about three days, and tested for anti-HIV activity, as above.

TABLE IX

Effect of Time Shaking in TFE on DAPTA Aggregation

| Time (hrs) | Percent Reduction in HIV Infection |
|---|---|
| 12 | 70 ± 4 |
| 24 | 100 ± 3 |
| 48 | 100 ± 3 |

Effect of Temperature of DAPTA Dissolved in TFE on Aggregation.

DAPTA, as above, was dissolved in 80% TFE, then shaken for about 24 hours at the indicated temperature(s) below in Table X. Again, the peptide was then evaporated or dried down, and resuspended in an aqueous solution, e.g., water for about three days, and tested for anti-HIV activity, as above.

TABLE X

Effect of Temperature of DAPTA Dissolved in TFE on Aggregation

| Temp. °C. | Percent Reduction in HIV Infection |
|---|---|
| Room Temp. | 70 ± 6 |
| 37 | 100 ± 5 |

EXAMPLE 9

Stabilization of DAPTA Using Various Formulations

Human elutriator purified monocytes were differentiated into macrophages by culture for 7 days (Ruff, M R, et al 2001). HIV-1 (ADA) strain was added with or without indicated peptide preparations and infection proceeded for 2 hrs at 37° C. Virus/peptide mixtures were removed by washing and cell cultures were maintained for 10 days. Supernatants were sampled and the level of HIV reverse transcriptase was determined as a measure of viral infection. Cultures were in triplicate and the mean and the standard deviation are presented.

Figure 6:
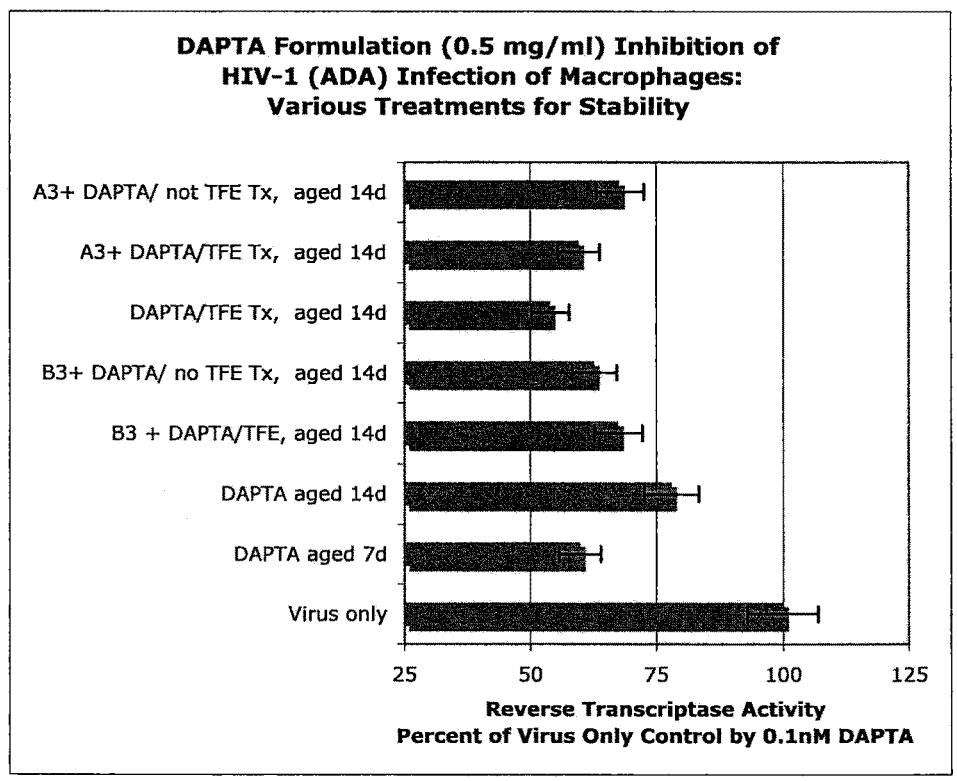
FIG. 6 is a graph showing DAPTA admixed with TFE and/or dodecyl maltoside ("A3"), or sucrose mono dodecanoate ("B3") inhibiting HIV infection in macrophages.

DAPTA is D-ala$^1$-peptide T-amide, GMP quality DAPTA was obtained from Bachem. Stability of the peptide formulations was determined by reconstituting peptide powder (0.5 mg/ml) in either 80% trifluoroethanol (TFE)/20% water which was then shaken overnight and taken to dryness in a speed-vac, "TFE Tx", or alternatively the peptide was not TFE treated. Peptide, TFE treated or not, was then reconstituted (0.5 mg/ml) in water or the indicated alkylglycoside (1 mg/ml) compositions containing 0.1% EDTA. Samples were then aged by storage at ambient temperature (ca 25° C.) for 14 days prior to antiviral testing. In FIG. 6, A3 denotes dodecyl maltoside and B3 denotes sucrose mono dodecanoate.

EXAMPLE 10

Quantitative Measurement of Protein Stabilization by Alkylsaccharides Using Light Scattering Measurements This study was performed to determine and document the effects of different alkylsaccharide surfactants having different anomer concentrations as described herein on the aggregation of various proteins in solution at 37° C. Recombinant human insulin (Humulin-R, manufactured by Eli Lilly) solutions containing alkylsaccharides having different concentrations of α and β anomers were prepared, along with an identical control protein solutions without alkylsaccharides. Solutions were incubated at 37° C. on a rotary platform shaker (LabLine thermoregulated shaker) at 150 rpm for up to 3 months. Protein aggregation was determined by measurements of light scatter using a Shimadzu RF-500 recording spectrofluorophotometer with both the excitation and emission wavelengths set at 500 nm. Measurements were taken on Day 0 and at various time intervals during an 88 day period.

Insulin Preparations. 25 ml solutions of Humulin-R (insulin) at 0.5 mg/ml and lysozyme at 1.0 mg/ml were prepared in citrate buffer at pH 7.6, without and with dodecyl maltoside having different concentrations of α and β anomer at 0.10% and 0.20% final surfactant concentrations, by dilution of Humulin-R U-100 (Lilly HI-210, 100 units/ml) recombinant human insulin stock solution at 4.0 mg/ml protein. A total of five solutions were prepared including: 1) a control solution containing insulin and buffer without dodecyl maltoside; 2) a solution having 0.10% final dodecyl maltoside concentration including less than 10% β anomer and greater than 90% α anomer; 3) a solution having 0.20% final dodecyl maltoside concentration including less than 10% β anomer and greater than 90% α anomer; 4) a solution having 0.10% final dodecyl maltoside concentration including greater than 99%β anomer and less than 1.0% α anomer; and 5) a solution having 0.20% final dodecyl maltoside concentration including greater than 99% β anomer and less than 1.0% α anomer. The final buffer composition was: 5 mM Citric Acid+0.1% EDTA, titrated with NaOH to pH 7.6. Each solution was stored in a 50 ml glass vial and capped with parafilm. Day 0 light scatter measurements were performed on the insulin samples at pH 7.6, and then the samples were re-sealed with parafilm and incubated at 37° C. with 150 rpm shaking.

Light Scatter Measurements. Light scatter was measured for each protein sample at selected time points during the three week study with a spectrofluorophotometer (Shimadzu model RF-1501). Both excitation and emission wavelengths were set to 500 nm, and samples were read in disposable cuvettes with a 1 cm path length. For each reading, the instrument was zeroed with 1 ml of the appropriate buffer, then an aliquot of protein sample was added, mixed by inverting multiple times, and the cuvette was checked for air bubbles before three stable readings were recorded. The spectrofluorophotometer was set for high sensitivity and the maximum possible reading was 1000 units. Insulin samples at Day 0 were measured with 50 ul aliquots, then with 10 μl aliquots for readings at subsequent time points. After light scatter readings were taken, each protein sample was re-sealed with parafilm and returned to 37° C. with 150 rpm shaking. The results are shown in the Table below and FIG. 7.

TABLE XI

Insulin Light Scatter Measurements (Average of 3 readings)

| Insulin pH 7.6 | Day 0 | Day 1 | Day 5 | Day 7 | Day 11 | Day 14 | Day 20 | Day 27 |
|---|---|---|---|---|---|---|---|---|
| Control | 0.4 | 200 | 1003 | 1003 | 1003 | 1003 | 1003 | 1003 |
| 0.1% dodecyl maltoside (less than 10% β anomer) | 2.2 | 2.2 | 1.5 | 3 | 3 | 1.7 | 68 | 1003 |

TABLE XI-continued

| Insulin Light Scatter Measurements (Average of 3 readings) | | | | | | | | |
|---|---|---|---|---|---|---|---|---|
| 0.2% dodecyl maltoside (less than 10% β anomer) | 5.2 | 5 | 4 | 3 | 5 | 0 | 300 | 1003 |
| 0.1% dodecyl maltoside (greater than 99% β anomer) | 0.1 | 2.9 | 1 | 0 | 2.2 | 1 | 0.5 | 1.6 |
| 0.2% dodecyl maltoside (greater than 99% β anomer) | 5 | 11 | 4.5 | 5 | 6 | 0 | 2.5 | 5 |

| Insulin pH 7.6 | Day 39 | Day 45 | Day 54 | Day 60 | Day 67 | Day 75 | Day 82 | Day 88 |
|---|---|---|---|---|---|---|---|---|
| Control | 1003 | 1003 | 1003 | 1003 | 1003 | 1003 | 1003 | 1003 |
| 0.1% dodecyl maltoside (less than 10% β anomer) | 1003 | 1003 | 1003 | 1003 | 1003 | 1003 | 1003 | 1003 |
| 0.2% dodecyl maltoside (less than 10% β anomer) | 1003 | 1003 | 1003 | 1003 | 1003 | 1003 | 1003 | 1003 |
| 0.1% dodecyl maltoside (greater than 99% β anomer) | 2 | 2 | 3 | 2.5 | 2 | 2 | 2 | 1003 |
| 0.2% dodecyl maltoside (greater than 99% β anomer) | 5 | 5 | 3 | 1 | 2 | 3 | 3 | 20 |

EXAMPLE 11

Stabilization of Parathyroid Hormone Analogs and Monoclonal IgG by alkylsaccharides This study demonstrated the effects of alkylsaccharide surfactants described herein on the aggregation of various proteins in solution using an accelerated testing protocol wherein the temperature is increased to 40° C. to speed the aggregation or denaturation process thus allowing for more rapid screening of the stabilization effects. This study examined the aggregation of Ostabolin C™ PTH 1-34 and a monoclonal antibody upon continuous agitation at 150 RPM on an orbital shaker thermostated at 40 deg. C., to determine the effectiveness of dodecylmaltoside in stabilizing each protein against aggregation.

Aqueous solutions of Ostabolin C™ (i.e., cyclic PTH 1-31) (Polypeptide Laboratories Inc.), Lot number PPL-CPTH310501A and PTH 1-34 (Polypeptide Laboratories Inc.), Lot number PPL-PTH340601 test articles were prepared as follows. Four mL (4 mL) aliquots of test article protein at a concentration of 2.25 mg/mL, prepared in pH 3.5, 10 mM glycine, 0.8% NaCl, 0.1% EDTA; and pH 5.0 10 mM acetate, 0.1% EDTA, are prepared, and split evenly into paired 2 mL aliquots in separate in glass serum vials.

To one vial of each paired protein solution is added 100 μL of 3.875% dodecyl maltoside in water (0.18% dodecylmaltoside final concentration). To a second vial is added 100 μL of sterile water for injection as a control. After a 50 μL aliquot is withdrawn from each test article to allow determination of light scatter, the test articles are placed on a thermostated orbital Lab-Line shaker at 150 RPM, 40° C.

Solutions were incubated at 40° C. on a rotary platform shaker (LabLine thermoregulated shaker) at 150 rpm for up to three weeks. Light scatter measurements at timed intervals were obtained as follows. A 50 μL aliquot of each test article is withdrawn and added to one mL of sterile water for injection in a disposable semi-micro fluorescence cuvette (Plastibrand® Model No. 7591). The cuvette is inverted 10 times and examined for the presence of air bubble inclusions. If air bubbles are present, the cuvette is gently tapped until the air bubbles are removed. Light scatter is determined using a Shimadzu Spectrofluorophotometer Model RF-1502 with both the excitation and emission monochromators set at 500 nm. Prior to each reading, the fluorometer was first zeroed on the corresponding cuvette containing the 1 ml of sterile water to eliminate variation in readings due to any variation in intrinsic fluorescence background arising from the disposable cuvettes.

Figure 13:
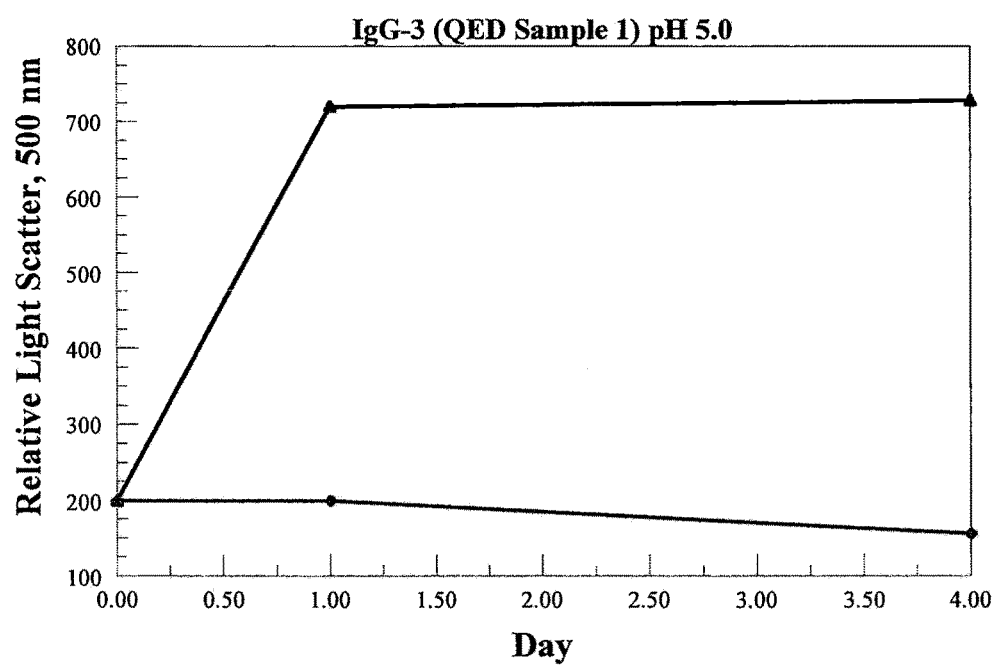
FIG. 13 is a graph showing light scatter readings for the polypeptide IgG-3 at pH 5.0, admixed with (lower line) and without (upper line) dodecyl maltoside (DDM).

Monoclonal IgG-3 (QED Bioscience Inc.) lot No. 050608 test articles containing 0.1% NaN3, 2.3 mg/mL antibody in 2.2mL (5.0 mg total) in pH 5.0 buffer, were diluted by addition of 2 mL of water, and pipetted 2 mL aliquots into paired glass serum vial. To one vial was added 66μL of 0.3875% Intravail™ A3 in water and to a second vial was added 66μL water (No Dodecyl maltoside Control). IgG samples were analyzed for light scatter without dilution and the light scatter results shown in Table XII and FIG. 13.

TABLE XII

Light Scatter Results of IgG3-1; pH5.0; Direct-No Dilution

| | Day/Date | No Intravail | With Intravail |
|---|---|---|---|
| Day 0 | 25-Feb-09 | 199 | 201 |
| Day 1 | 26-Feb-09 | 720 | 199 |
| Day 4 | 27-Feb-09 | 728 | 156 |

The light scatter results for results for Ostabolin C™ (i.e., cyclic PTH 1-31) and PTH 1-34 are shown in FIGS. 8, 9, 10, 11 and 12.

EXAMPLE 12

Stabilization of PTH 1-34 by Alkylsaccharides at 37° C.

Figure 12:
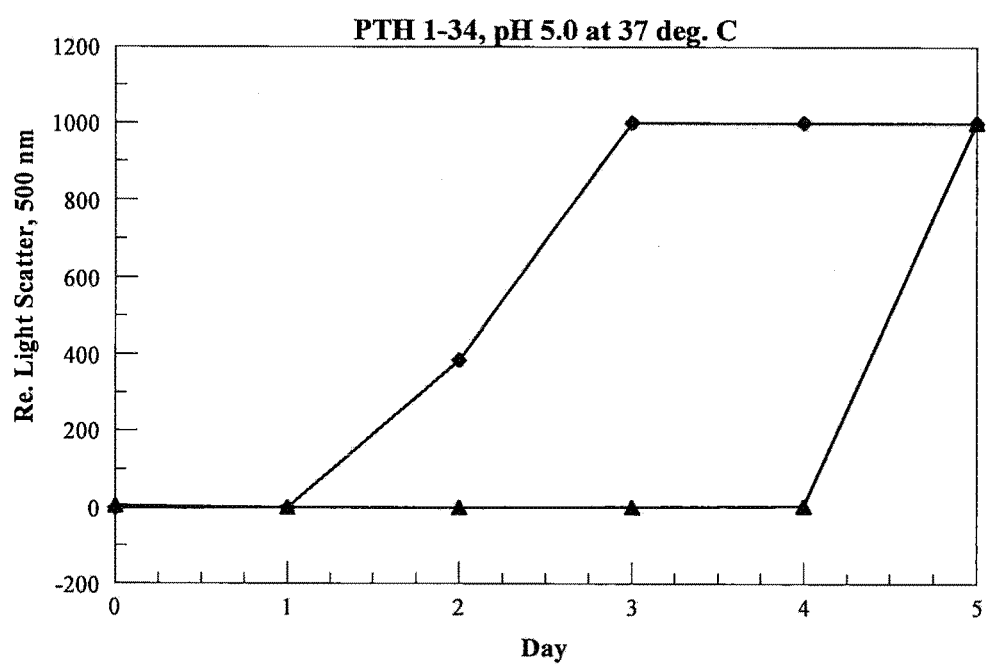
FIG. 12 is a graph showing light scatter readings for the polypeptide PTH 1-34 at pH 5.0, admixed with (lower line) and without (upper line) dodecyl maltoside (DDM).

The study of PTH 1-34 was then repeated as described above except that the temperature during agitation was reduced to 37° C. The results are shown in FIG. 12. PTH 1-34 is significantly more stable at 37° C. compare to the results obtained in the accelerated stability study of Example 11 conducted at 40° C.

EXAMPLE 13

Stabilization of Interferon and an Amylin Derived Peptide By Alkyl Saccharides

This study demonstrated the effects of alkylsaccharide surfactants described herein on the aggregation of interferons, an amylin related peptide (Pramlintide®) and calcitonin (Fortical®) upon continuous agitation at 150 RPM on an orbital shaker thermostated at 37° C. to determine the effectiveness of dodecylmaltoside in stabilizing each protein against aggregation.

Aqueous solutions of beta interferon 1a (Rebif®), Lot number Y09A2635, beta interferon 1b (Betaseron®), Lot number YA0549A, amylin related peptide (Pramlintide®), Lot number 905182, and Fortical® salmon calcitonin nasal spray, Lot number 249793 test articles were prepared as follows.

One mL aliquots of Rebif® beta interferon 1a, Betaseron® beta interferon 1b, salmon calcitonin, and Pramlintide® are placed in glass serum vials. To one vial of each protein solution is added 50 µL of 4.2% Dodecyl maltoside A3 in water (0.2% Dodecyl maltoside final conc.). To a second vial is added 50 µL of sterile water for injection as a control. After a 25 µL aliquot is withdrawn from each test article to allow determination of light scatter, the test articles are placed on a thermostated orbital Lab-Line shaker at 150 RPM, 37° C.

Light scatter measurements at timed intervals were obtained as follows. A 25 µL aliquot of each test article is withdrawn and added to one mL of sterile water for injection in a disposable semi-micro fluorescence cuvette (Plastibrand® Model No. 7591). The cuvette is inverted 10 times and examined for the presence of air bubble inclusions. If air bubbles are present, the cuvette is gently tapped until the air bubbles are removed. Light scatter is determined using a Shimadzu Spectrofluorophotometer Model RF-1502 with both the excitation and emission monochromators set at 500 nm. Prior to each reading, the fluorometer was first zeroed on the corresponding cuvette containing the 1 ml of sterile water to eliminate variation in readings due to any variation in intrinsic fluorescence background arising from the disposable cuvettes.

Figure 14:
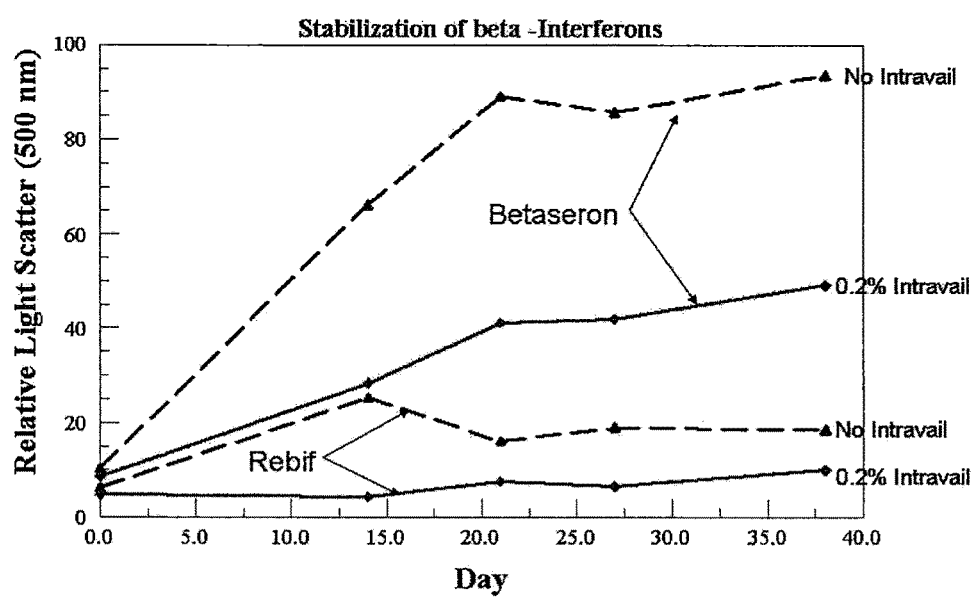
FIG. 14 is a graph showing light scatter readings for beta interferon polypeptides admixed with and without dodecyl maltoside (DDM).
Figure 15:
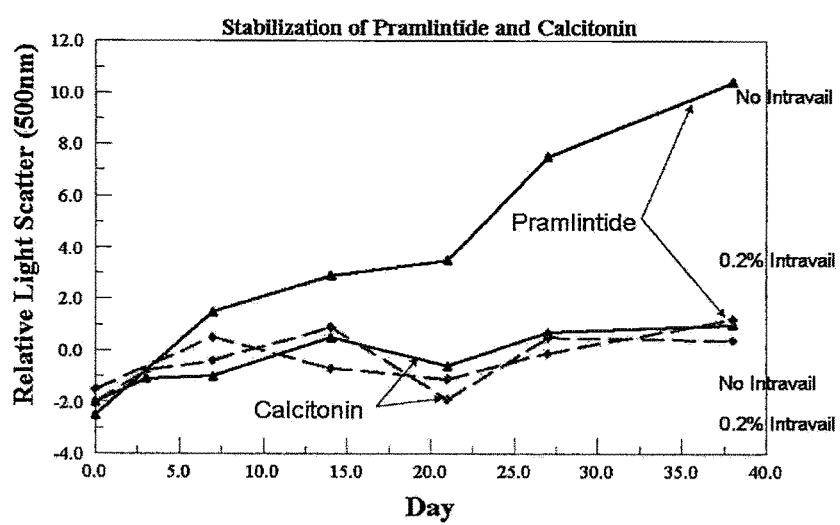
FIG. 15 is a graph showing light scatter readings for the polypeptides Pramlintide® and calcitonin admixed with and without dodecyl maltoside (DDM).

The results are shown in FIGS. 14 and 15. Both interferons showed aggregation as indicated by increased light scatter, with Betaseron® showing a much larger increase in light scatter. Increase in light scatter was more or less linear over the 38 day test period. Betaseron® exhibits the greatest stabilization effect by 0.2% Dodecyl maltoside/ProTek™ A3 over the 38 day test period. Rebif® showed a smaller but consistent trend toward greater stabilization by 0.2% Dodecyl maltoside/ProTek™ A3. Pramlintide® showed significant stabilization (approx. 5-fold) in the presence of 0.2% Dodecyl maltoside/ProTek™ A3. Calcitonin appeared to be stable either in the presence or absence of excipient as measured by light scatter at 500 nm. Both interferons showed a 2-fold reduction in light scatter in the presence of Dodecyl maltoside® A3. Since earlier studies with insulin and growth hormone demonstrated the same equivalent and maximum stabilization against aggregation with Dodecyl maltoside concentrations as low as 0.0625% wt/vol., lower concentrations may prove equally effective with the beta interferons as well.

REFERENCES

Ainge G, Bowles, J. A., McCormick, S. G., et al. 1994. Lack of deleterious effects of corticosteroid sprays containing benzalkonium chloride on nasal ciliated epithelium. Drug Invest 8:127-33.

Andya J, Maa, Y F, et al. 1999. The effect of formulation excipients on protein stability and aerosol performance of spray-dried powders of a recombinant humanized anti-IgE monoclonal antibody. Pharm Res 16(3):350-8.

Arakawa, T. and Timasheff, S. N. Stabilization of protein structure by sugars. Biochemistry, 21 (1982) 6536 6544.

Arakawa, T. and Timasheff, S. N., Stabilization of proteins by osmolytes. Biophys. J., 47 (1985) 411 414.

Berg O H, Henriksen, R. N., and Steinsvag, S. K. 1995. The effect of a benzalkonium chloride-containing nasal spray on human respiratory mucosa in vitro as a function of concentration and time of action. Pharmacol Toxicol 76:245-9.

Braat J P, Ainge, G., Bowles, J. A., et al. 1995. The lack of effect of benzalkonium chloride on the cilia of the nasal mucosa in patients with perennial allergic rhinitis: A combined functional, light, scanning and transmission electron microscopy study. Clin Exp Allergy 25:957-65.

Brenneman, D. E., J. M. Buzy, M. R. Ruff, and C. B. Pert. 1988. Peptide T sequences prevent neuronal cell death produced by the envelope protein (gp120) of the human immunodeficiency virus. *Drug Devel Res.* 15:361-369.

Bridge T P, Heseltine P N, Parker E S, Eaton E, Ingraham L J, Gill M, Ruff M, Pert C B, Goodwin F K. 1989. Improvement in AIDS patients on peptide T. Lancet 2(8656):226-7.

Casadevall N, et al. 2002. Pure red-cell aplasia and anti-erythropoietin antibodies in patients treated with recombinant erythropoietin. N Engl J Med 346(7):469-75.

Chawla, A. S., Hinberg, I., Blais, P. and Johnson, D. Aggregation of insulin, containing surfactants, in contact with different materials. Diabetes 34 (1985) 420-24.

Clodfelter. 1998. Effects of non-covalent self-association on the subcutaneous absorption of a therapeutic peptide Pharm Res 15 254-62.

Clodfelter D K, Pekar A H, Rebhun D M, Destrampe K A, Havel H A, Myers S R, Brader M L. 1998. Effects of non-covalent self-association on the subcutaneous absorption of a therapeutic peptide. Pharm Res 15(2):254-62.

DePalma A. Jan. 15, 2006. BioProcessing: Improving Stability While Adding Value. Genetic Eng. News 26,(2).

Graf P, Enerdal, J., and Hallen, H.1999. Ten days' use of oxymetazoline nasal spray with or without benzalkonium chloride in patients with vasomotor rhinitis. Arch Otolaryngol Head Neck Surg 125:1128-32.

Hermeling S, Schellekens H, Maas C, Gebbink M F, Crommelin D J, Jiskoot W. 2006. Antibody response to aggregated human interferon alpha2b in wild-type and transgenic immune tolerant mice depends on type and level of aggregation. J Pharm Sci.

Heseltine, P. N., K. Goodkin, J. H. Atkinson, B. Vitiello, J. Rochon, R. K. Heaton, E. M. Eaton, F. L. Wilkie, E. Sobel, S. J. Brown, D. Feaster, L. Schneider, W. L. Goldschmidts, and E. S. Stover. 1998. Randomized double-blind placebo-controlled trial of peptide T for HIV-associated cognitive impairment. *Arch Neurol.* 55:41-51.

Holm A F, Fokkens, W. J., Godthelp, T., et al. 1998. A 1-year placebo-controlled study of intranasal fluticasone propionate aqueous nasal spray in patients with perennial allergic rhinitis: A safety and biopsy study. Clin Otolaryngol 23:69-73.

King H D, Dubowchik G M, Mastalerz H, Willner D, Hofstead S J, Firestone R A, Lasch S J, Trail P A. 2002. Monoclonal antibody conjugates of doxorubicin prepared with branched peptide linkers: inhibition of aggregation by methoxytriethyleneglycol chains. J Med Chem 45(19):4336-43.

Klossek J M, Laliberte, F., Laliberte, M. F. et al. 2001. Local safety of intranasal triamcinolone acetonide: clinical and histological aspects of nasal mucosa in the long term treatment of perennial allergic rhinitis. Rhinology 39:17-22.

Kosten T R, Rosen M I, McMahon T L, Bridge T P, O'Malley S S, Pearsall R, O'Connor P G. 1997. Treatment of early AIDS dementia in intravenous drug users: high versus low dose peptide T. Am J Drug Alcohol Abuse 23(4):543-53.

Lange B, Lukat, K. F., and Bachert, C. 2004. Local tolerability of a benzalkonium chloride-containing homeopathic nasal spray. Allergologie 27(3):102.

MacFadden D K and Doob P R. 1991. Role of peptide T in palliation of HIV-1 related painful peripheral neuropathy; 7th Intl AIDS Conference, Florence Italy—Jun. 16-21, 1991 (Sponsor:International AIDS Society) Abstract No. W. B.2173).

Marple B, Roland, P., and Benninger, M. 2004. Safety review of benzalkonium chloride used as a preservative in intranasal solutions: An overview of conflicting data and opinions. Otolaryngology-Head and Neck Surgery 130(1):131-141.

McMahon C, Darby, Y., Ryan, R., et al. 1997. Immediate and short-term effects of benzalkonium chloride on the human nasal mucosa in vivo. Clin Otolaryngol 22:318-22.

Pert C B, Ruff M R. 1986. Peptide T[4-8]: a pentapeptide sequence in the AIDS virus envelope which blocks infectivity is essentially conserved across nine isolates. Clin Neuropharmacol 9 Suppl 4:482-4.

Pert C B, Ruff M R, Hill J M. 1988. AIDS as a neuropeptide disorder: peptide T, VIP, and the HIV receptor. Psychopharmacol Bull 24(3):315-9.

Pert et al. 2005. Chemokines receptor 5 antagonist D-ala Peptide T amide reduces microglia and astrocyte activation within the hippocampus in a neuroinflammatory rat model of Alzheimer's disease Neuroscience 134:671-676.

Pezron I, Mitra R, Pal D, Mitra A K. 2002. Insulin aggregation and asymmetric transport across human bronchial epithelial cell monolayers (Calu-3). J Pharm Sci 91(4):1135-46.

Polianova, Maria T., Gifford Leoung, Scott Strang, Candace B. Pert, Francis W. Ruscetti, Michael R. Ruff. 2003. Anti-viral and immunological benefits in HIV patients receiving peptide T. Peptides 24(7):1093-8.

Porter W R, Staack H, Brandt K, Manning M C. 1993. Thermal stability of low molecular weight urokinase during heat treatment. I. Effects of protein concentration, pH and ionic strength. Thromb Res 71(4):265-79.

Purohit V S, Middaugh C R, Balasubramanian S V. 2006. Influence of aggregation on immunogenicity of recombinant human Factor VIII in hemophilia A mice. Pharm Sci 95(2): 358-71.

Riechelmann H, Deutschle, T., Stuhlmiller, A., Gronau, S., Burner, H. 2004. Nasal toxicity of benzalkonium chloride. American Journal of Rhinology 18 (5):291-299.

Roccatano et al. 2002. Mechanism by which 2,2,2-trifluoroethanol/water mixtures stabilize secondary-structure formation in peptides: A molecular dynamics study PNAS 99(19):12179-12184.

Raychaudhuria, et al. 1999 Immunomodulatory effects of Peptide T on Th 1/Th 2 Cytokines. International Journal of Immunopharmacology 21:609-615.

Redwine, L S Rone, J D, Pert, C B, Nixon, R., Vance, M. Sandler, B., Lumpkin, M D, and, Ruff, M R. 1999. GP120 (V2)-Derived Peptide T Blocks GP120/CCR5 Chemokine Receptor Mediated Chemotaxis. Clinical Immunology. 93:124.

Roy S, Jung R, Kerwin B A, Randolph T W, Carpenter J F. 2005. Effects of benzyl alcohol on aggregation of recombinant human interleukin-1-receptor antagonist in reconstituted lyophilized formulations. J Pharm Sci 94(2):382-96.

Ruff M R, Hallberg P L, Hill J M, Pert C B. 1987. Peptide T[4-8] is core HIV envelope sequence required for CD4 receptor attachment. Lancet 2(8561):751.

Ruff M R, Melendez-Guerrero L M, Yang Q E, Ho W Z, Mikovits J W, Pert C B, Ruscetti F A. 2001. Peptide T inhibits HIV-1 infection mediated by the chemokine receptor-5 (CCR5). Antiviral Res 52(1):63-75.

Ruff M R, Polianova M, Yang Q E, Leoung G S, Ruscetti F W, Pert C B. 2003. Update on D-ala-peptide T-amide (DAPTA): a viral entry inhibitor that blocks CCR5 chemokine receptors. Curr HIV Res 1(1):51-67.

Ruff M R, Smith C, Kingan T, Jaffe H, Heseltine P, Gill M A, Mayer K, Pert C B, Bridge T P. 1991. Pharmacokinetics of peptide T in patients with acquired immunodeficiency syndrome (AIDS). Prog Neuropsychopharmacol Biol Psychiatry 15(6):791-801.

Sato, S., Ebert, C. D. and Kim, S. W. 1983. Prevention of insulin self-association and surface adsorption. J. Pharm. Sci., 72:228-232.

Simpson, D. M., D. Dorfman, R. K. Olney, G. McKinley, J. Dobkin, Y. So, J. Berger, M. B. Ferdon, and B. Friedman. 1996. Peptide T in the treatment of painful distal neuropathy associated with AIDS: results of a placebo-controlled trial. The Peptide T Neuropathy Study Group. *Neurology* 47:1254-1259.

Sluzky V, Tamada J A, Klibanov A M, Langer R. 1991. Kinetics of insulin aggregation in aqueous solutions upon agitation in the presence of hydrophobic surfaces. Proc Natl Acad Sci USA 88(21):9377-81.

Sonnichsen F D, Van Eyk J E, Hodges R S, Sykes B D. 1992. Effect of trifluoroethanol on protein secondary structure: an NMR and CD study using a synthetic actin peptide, Biochemistry, 31(37)8790-8798.

Thurow, H. and Geisen, K. 1984. Stabilization of dissolved proteins against denaturation at hydrophobic surfaces. Diabetol., 27:212-218.

Wright J, et al. 2005. Identification of factors that contribute to recombinant AAV2 particle aggregation and methods to prevent its occurrence during vector purification and formulation. Mol Ther 12(1):171-8.

Zhang M Z, Wen J, Arakawa T, Prestrelski S J. 1995. A new strategy for enhancing the stability of lyophilized protein: the effect of the reconstitution medium on keratinocyte growth factor. Pharm Res 12(10):1447-52.

Although the present process has been described with reference to specific details of certain embodiments thereof in the above examples, it will be understood that modifications and variations are encompassed within the spirit and scope of the invention. Accordingly, the invention is limited only by the following claims.

What is claimed is:

1. A pharmaceutical composition for increasing stability, reducing aggregation or reducing immunogenicity of a monoclonal antibody comprising: a monoclonal antibody; and a stabilizing agent comprising at least one alkylglycoside, wherein the alkylglycoside is selected from: octyl-, nonyl-, decyl-, undecyl-, dodecyl-, tridecyl-, tetradecyl, pentadecyl-, hexadecyl-, heptadecyl-, and octadecyl-D-maltoside and D-glucoside; octyl-, nonyl-, decyl-, undecyl-, dodecyl-, tridecyl-, tetradecyl, pentadecyl-, hexadecyl-, heptadecyl-, and octadecyl-maltoside; octyl-, nonyl-, decyl-, undecyl-, dodecyl-, tridecyl-, tetradecyl, pentadecyl-, hexadecyl-, heptadecyl-, and octadecyl-glucoside; octyl-, nonyl-, decyl-, undecyl-, dodecyl-, tridecyl-, tetradecyl, pentadecyl-, hexadecyl-, heptadecyl-, and octadecyl-sucroside; an alkyl thiomaltoside selected from heptyl, octyl, dodecyl-, tridecyl-, and tetradecyl-beta-D-thiomaltoside; an alkyl thioglucoside selected from heptyl- and octyl- 1-thio beta- and beta-D-glucopyranoside; an alkyl maltotrioside; a long chain aliphatic carbonic acid amide of sucrose amino-alkyl ether; a derivative of palatinose and isomaltamine linked by amide linkage to an alkyl chain; a derivative of isomaltamine linked by urea to an alkyl chain; a long chain aliphatic carbonic acid ureide of sucrose amino-alkyl ether; and a long chain aliphatic carbonic acid amide of sucrose amino-alkyl ether.

2. The composition of claim 1, wherein the monoclonal antibody is selected from the group consisting of abagovomab, afelimomab, anatumomab mafenatox, arcitumomab, bectumomab, besilesomab, capromab, edobacomab, edrecolomab, elsilimomab, enlimomab, enlimomab pegol, epitumomab cituxetan, ibritumomab tiuxetan, imciromab, inolimomab, mitumomab, oregovmab, satumomab, sulesomab, technetium ($^{99m}$Tc) nofetumomab merpentan, tosituromomab, vepalimomab, zolimomab aritox, adalimumab, adecatumumab, belimumab, bertilimumab, denosumab, efungumab, golimumab, ipilimumab, iratumumab, lerdelimumab, lexatumumab, mapatumumab, metelimumab, ofatumumab, panitumumab, pritumumab, raxibacumab, sevirumab, stamulumab, ticilimumab, tuvirumab, votumumab, zalutumumab, zanolimumab, abciximab, basiliximab, bavituximab, cetuximab, ecromeximab, galiximab, infliximab, keliximab, lumiliximab, pagibaximab, priliximab, rituximab, teneliximab, volociximab, alemtuzumab, apolizumab, aselizumab, bapineuzumab, bevacizumab, bivatuzumab, cantuzumab mertansine, certolizumab pegol, daclizumab, eculizumab, efalizurnab, epratuzumab, fontolizumab, gemtuzumab, inotuzumab ozogamicin, labetuzumab, lintuzumab, matuzumab, mepolizumab, motavizumab, natalizumab, nimotuzumab, ocrelizumab, omalizumab, palivizumab, pascolizumab, pertuzumab, pexelizumab, ranibizumab, reslizumab, rovelizumab, ruplizumab, sibrotuzumab, siplizumab, sontuzumab, tadocizumab, talizumab, tefibazumab, tocilizumab, toralizumab, trastuzumab, tucotuzumab celmoleukin, urtoxazumab, visilizumab, yttrium$^{90Y}$ tacatuzumab tetraxetan, and IgG.

3. The composition of claim 2, wherein the monoclonal antibody is IgG.

4. The composition of claim 1, further comprising a buffering agent.

5. The composition of claim 1, wherein the alkylglycoside has an alkyl chain and wherein the alkyl chain has between about 8 to 16 carbon atoms.

6. The composition of claim 1, wherein the alkylglycoside is selected from the group consisting of octyl maltoside, octyl glucoside, octyl sucroside, decyl-D-glucoside, decyl-D-maltoside, decyl-sucroside, octyl-D-glucoside, octyl-D-maltoside, dodecyl maltoside, tridecyl maltoside, tetradecyl maltoside, sucrose mono-dodecanoate, sucrose mono-tridecanoate, and sucrose mono-tetradecanoate.

7. The composition of claim 1, wherein the alkylglycoside has a critical micelle concentration (CMC) of less than about 1 mM.

8. The composition of claim 7, wherein the alkylglycoside has a CMC of less than about 0.5 mM.

9. The composition of claim 1, further comprising a mucosal delivery-enhancing agent selected from the group consisting of an aggregation inhibitory agent, a charge-modifying agent, a pH control agent, a degradative enzyme inhibitory agent, a mucolytic or mucus clearing agent, a chitosan, and a ciliostatic agent.

10. The composition of claim 9, wherein the mucosal delivery-enhancing agent is a chitosan.

11. The composition of claim 9, wherein the mucosal delivery-enhancing agent is a ciliostatic agent.

12. The composition of claim 1, further comprising benzalkonium chloride or chloroethanol.

13. The composition of claim 1, further comprising a membrane penetration-enhancing agent selected from the group consisting of a surfactant, a bile salt, a phospholipid additive, a mixed micelle, a liposome, a carrier, an alcohol, an enamine, a nitric oxide donor compound, a long-chain amphipathic molecule, a small hydrophobic penetration enhancer, a sodium or a salicylic acid derivative, a glycerol ester of acetoacetic acid, a cyclodextrin or beta-cyclodextrin derivative, a medium-chain fatty acid, a chelating agent, an amino acid or salt thereof, an N-acetylamino acid or salt thereof, an enzyme degradative to a selected membrane component and any combination thereof.

14. The composition of claim 1, further comprising a modulatory agent of epithelial junction physiology.

15. The composition of claim 1, further comprising a vasodilator agent.

16. The composition of claim 1, further comprising a selective transport-enhancing agent.

17. The composition of claim 1, wherein the composition is in a lyophilized form.

18. The composition of claim 17, wherein the lyophilized composition retains greater than 50% biological activity upon reconstitution.

19. The composition of claim 1, wherein the composition is stable to denaturation as determined by lack of increased light scatter for at least one week upon agitation at 150 RPM at temperatures from about 25 to 37 degrees Celsius.

20. The composition of claim 19, wherein the composition is stable to denaturation as determined by lack of increased light scatter for at least two weeks upon agitation at 150 RPM at temperatures from about 25 to 37 degrees Celsius.

21. The composition of claim 1, wherein the composition is stable to denaturation as determined by lack of increased light scatter for at least one year when stored at about 4 degrees Celsius.

22. The composition of claim 1, wherein the stability of the composition is determined by determining the bioactivity of the monoclonal antibody in an in vivo or in vitro assay.

23. The composition of claim 18, wherein the lyophilized composition further comprises a bulking agent selected from the group consisting of albumin, collagen, alginate, and mannitol.

24. The composition of claim 17, wherein the lyophilized composition is reconstituted prior to administering to a mammalian subject.

25. The composition of claim 1, wherein the composition is formulated for parenteral, intransal, pulmonary, or buccal delivery.

26. A method for increasing the stability of a monoclonal antibody comprising: admixing the monoclonal antibody, a stabilizing agent and a buffering agent to form a composition, wherein the stabilizing agent is at least one alkylglycoside surfactant, thereby increasing the stability of the monoclonal antibody, wherein the alkylglycoside is selected from: octyl-, nonyl-, decyl-, undecyl-, dodecyl-, tridecyl-, tetradecyl, pentadecyl-, hexadecyl-, heptadecyl-, and octadecyl-D-maltoside and D-glucoside; octyl-, nonyl-, decyl-, undecyl-, dodecyl-, tridecyl-, tetradecyl, pentadecyl-, hexadecyl-, heptadecyl-, and octadecyl-maltoside; octyl-, nonyl-, decyl-, undecyl-, dodecyl-, tridecyl-, tetradecyl, pentadecyl-, hexadecyl-, heptadecyl-, and octadecyl-glucoside; octyl-, nonyl-, decyl-, undecyl-, dodecyl-, tridecyl-, tetradecyl, pentadecyl-, hexadecyl-, heptadecyl-, and octadecyl-sucroside; an alkyl thiomaltoside selected from heptyl, octyl, dodecyl-, tridecyl-, and tetradecyl-beta-D-thiomaltoside; an alkyl thioglucoside selected from heptyl- and octyl- 1-thio beta- and beta-D-glucopyranoside; an alkyl maltotrioside; a long chain aliphatic carbonic acid amide of sucrose amino-alkyl ether; a derivative of palatinose and isomaltamine linked by amide linkage to an alkyl chain; a derivative of isomaltamine linked by urea to an alkyl chain; a long chain aliphatic carbonic acid ureide of sucrose amino-alkyl ether; and a long chain aliphatic carbonic acid amide of sucrose amino-alkyl ether.

27. The method of claim 26, wherein the monoclonal antibody is selected from the group consisting of: abagovomab, afelimomab, anatumomab mafenatox, arcitumomab, bectumomab, besilesomab, capromab, edobacomab, edrecolomab, elsilimomab, enlimomab, enlimomab pegol, epitumomab cituxetan, ibritumomab tiuxetan, imciromab, inolimomab, mitumomab, oregovomab, satumomab, sulesomab, technetium ($^{99}$mTc) nofetumomab merpentan, tositumomab, vepalimomab, zolimomab aritox, adalimumab, adecatumumab, belimumab, bertilimumab, denosumab, efungumab, golimumab, ipilimumab, iratumumab, lerdelimumab, lexatumumab, mapatumumab, metelimumab, ofatumumab, panitumumab, pritumumab, raxibacumab, sevirumab, stamulumab, ticilimumab, tuvirumab, votumumab, zalutumumab, zanolimumab, abciximab, basiliximab, bavituximab, cetuximaba ecromeximab, galiximab, infliximab, keliximab, lumiliximab, pagibaximab, priliximab, rituximab, teneliximab, volociximab, alemtuzumab, apolizumab, aselizumab, bapineuzumab, bevacizumab, bivatuzumab, cantuzumab mertansine, certolizumab pegol, daclizumab, eculizumab, efalizumab, epratuzumab, fontolizumab, gemtuzumab, inotuzumab ozogamicin, labetuzumab, lintuzumab, matuzumab, mepolizumab, motavizumab, natalizumab, nimotuzumab, ocrelizumab, omalizumab, palivizumab, pascolizumab, pertuzumab, pexelizumab, ranibizumab, reslizumab, rovelizumab, ruplizumab, sibrotuzumab, siplizumab, sontuzumab, tadocizumab, talizumab, tefibazumab, tocilizumab, toralizumab, trastuzumab, tucotuzumab celmoleukin, urtoxazumab, visilizumab , yttrium$^{90Y}$ tacatuzumab tetraxetan, IgG-1, IgG-2, IgG-3, and IgG-4.

28. The method of claim 27, wherein monoclonal antibody is IgG-3.

29. The method of claim 26, wherein the alkylglycoside is selected from the group consisting of octyl maltoside, octyl glucoside, octyl sucroside, decyl-D-glucoside, decyl-D-maltoside, decyl-sucroside, octyl-D-glucoside, octyl-D-maltoside, dodecyl maltoside, tridecyl maltoside, tetradecyl maltoside, sucrose mono-dodecanoate, sucrose mono-tridecanoate, and sucrose mono-tetradecanoate.

30. The method of claim 26, wherein the alkylglycoside has a critical micelle concentration (CMC) of less than about 1 mM.

31. The method of claim 30, wherein the alkylglycoside has a CMC of less than about 0.5 mM.

32. The method of claim 26, wherein the composition further comprises a mucosal delivery-enhancing agent selected from the group consisting of an aggregation inhibitory agent, a charge-modifying agent, a pH control agent, a degradative enzyme inhibitory agent, a mucolytic or mucus clearing agent, a chitosan, and a ciliostatic agent.

33. The method of claim 32, wherein the mucosal delivery-enhancing agent is a chitosan.

34. The method of claim 32, wherein the mucosal delivery-enhancing agent is a ciliostatic agent.

35. The method of claim 26, wherein the composition further comprises benzalkonium chloride or chloroethanol.

36. The method of claim 26, wherein the composition further comprises a membrane penetration-enhancing agent selected from the group consisting of a surfactant, a bile salt, a phospholipid additive, a mixed micelle, a liposome, a carrier, an alcohol, an enamine, a nitric oxide donor compound, a long-chain amphipathic molecule, a small hydrophobic penetration enhancer, a sodium or a salicylic acid derivative, a glycerol ester of acetoacetic acid, a cyclodextrin or beta-cyclodextrin derivative, a medium-chain fatty acid, a chelating agent, an amino acid or salt thereof, an N-acetylamino acid or salt thereof, an enzyme degradative to a selected membrane component and any combination thereof.

37. The method of claim 26, wherein the composition further comprises a modulatory agent of epithelial junction physiology.

38. The method of claim 26, wherein the composition further comprises a vasodilator agent.

39. The method of claim 26, wherein the composition further comprises a selective transport-enhancing agent.

40. The method of claim 26, wherein the composition is in a lyophilized form.

41. The method of claim 40, wherein the composition retains greater than 50% biological activity upon reconstitution.

42. The method of claim 26, wherein the composition is stable to denaturation as determined by lack of increased light scatter for least one week when stored at temperatures from about 25 to 37 degrees Celsius.

43. The method of claim 42, wherein the composition is stable to denaturation as determined by lack of increased light scatter for at least two weeks when stored at temperatures from about 25 to 37 degrees Celsius.

44. The method of claim 26, wherein the composition is stable to denaturation as determined by lack of increased light scatter for at least one year when stored at about 4 degrees Celsius.

45. The method of claim 26, wherein the stability of the composition is determined by determining the bioactivity of the monoclonal antibody in an in vivo or in vitro assay.

46. The method of claim 26, wherein the composition further comprises a bulking agent selected from the group consisting of albumin, collagen, alginate, and mannitol.

47. The method of claim 40, wherein the composition is reconstituted prior to administering to a mammalian subject.

48. The method of claim 26, wherein the stability of the composition is determined by light scatter.

* * * * *

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic construct

<400> SEQUENCE: 1

Thr Thr Ser Tyr Thr
1               5